United States Patent
Keller et al.

(10) Patent No.: US 11,078,494 B2
(45) Date of Patent: *Aug. 3, 2021

(54) VECTOR FOR TARGETING THE HUMAN ROSA26 GENE

(71) Applicant: Icahn School of Medicine at Mount Sinai, New York, NY (US)

(72) Inventors: Gordon Keller, Toronto (CA); Stefan Irion, Toronto (CA); Herve Luche, Ulm (DE); Paul Gadue, New York, NY (US); Hans J. Fehling, Ulm (DE)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/664,291

(22) Filed: Oct. 25, 2019

(65) Prior Publication Data

US 2020/0071719 A1    Mar. 5, 2020

Related U.S. Application Data

(60) Continuation of application No. 15/331,299, filed on Oct. 21, 2016, now abandoned, which is a division of
(Continued)

(51) Int. Cl.
*C12N 15/00* (2006.01)
*C12N 15/85* (2006.01)
(Continued)

(52) U.S. Cl.
CPC .......... *C12N 15/85* (2013.01); *C07K 14/4702* (2013.01); *C12N 5/0606* (2013.01);
(Continued)

(58) Field of Classification Search
CPC ............................. C12N 15/85; C12N 15/907
(Continued)

(56) References Cited

U.S. PATENT DOCUMENTS 6,461,864 B1    10/2002  Soriano et al.
7,473,557 B2    1/2009   Economides et al.
(Continued)

FOREIGN PATENT DOCUMENTS

CN    1341639       *  9/2000
CN    1341639 A        3/2002
(Continued)

OTHER PUBLICATIONS

Dacquin (Dev. Dynamics, 2002, vol. 224, p. 245-251).*
(Continued)

*Primary Examiner* — Michael C Wilson
(74) *Attorney, Agent, or Firm* — Fox Rothschild LLP

(57) ABSTRACT

The invention provides a method for generating a transgenic eukaryotic cell population having a modified human Rosa26 locus, which method includes introducing a functional DNA sequence into the human Rosa26 locus of starting eukaryotic cells. Also provided are targeting vectors useful in the method, as well as a cell population and a transgenic non-human animal comprising a modified human Rosa26 locus. Finally, the invention provides an isolated DNA sequence corresponding to the human Rosa26 locus.

11 Claims, 10 Drawing Sheets

Specification includes a Sequence Listing.

Related U.S. Application Data application No. 14/717,472, filed on May 20, 2015, now Pat. No. 9,481,896, which is a continuation of application No. 12/523,632, filed as application No. PCT/US2008/000666 on Jan. 18, 2008, now Pat. No. 9,062,122.

(60) Provisional application No. 60/881,226, filed on Jan. 19, 2007.

(51) Int. Cl.
  *C12N 5/0735* (2010.01)
  *C07K 14/47* (2006.01)
  *C12N 15/90* (2006.01)

(52) U.S. Cl.
  CPC ........ *C12N 15/907* (2013.01); *A01K 2207/15* (2013.01); *A01K 2217/00* (2013.01); *C12N 2510/00* (2013.01); *C12N 2800/30* (2013.01); *C12N 2830/85* (2013.01); *C12N 2840/44* (2013.01)

(58) Field of Classification Search
  USPC .............................................. 435/320.1, 325
  See application file for complete search history.

(56) References Cited

U.S. PATENT DOCUMENTS

| | | | |
|---|---|---|---|
| 9,062,122 | B2 | 6/2015 | Keller et al. |
| 9,481,896 | B2 | 11/2016 | Keller et al. |
| 2006/0205077 | A1* | 9/2006 | Schwenk ........... A01K 67/0275 435/455 |
| 2007/0134796 | A1 | 6/2007 | Holmes et al. |
| 2009/0210955 | A1 | 8/2009 | Seibler et al. |

FOREIGN PATENT DOCUMENTS

| | | | |
|---|---|---|---|
| WO | 1999053017 | A2 | 10/1999 |
| WO | WO 1999/053017 | * | 10/1999 |
| WO | 2002/098217 | A1 | 12/2002 |
| WO | WO 2002/098217 | * | 12/2002 |
| WO | 03020743 | A1 | 3/2003 |
| WO | 2003020743 | A1 | 3/2003 |
| WO | WO 2003/020743 | * | 3/2003 |
| WO | 2004063381 | A1 | 7/2004 |
| WO | 2006131543 | A1 | 12/2006 |
| WO | 2007014275 | A2 | 2/2007 |

OTHER PUBLICATIONS

Moses (Genesis, 2001, vol. 31, p. 176-180).*
Oumard (Cytotechnology, 2006, vol. 50, p. 93-108).*
Mao Yumin CN 1341639 translation.*
Zambrowicz, et al. Disruption of overlapping transcripts in the ROSA beta-geo 26 gene trap strain leads to widespread expression of beta-galactosidase in mouse embryos and hematopoietic cells. PNAS 94: 3789-3794. (1997).
Zambrowicz, et al. Disruption of overlapping transcripts in the ROSA beta-geo 26 gene trap strain leads to widespread expression of beta-galactosidase inmouse embryos and hematopoietic cells. Proc. Natl. Acad. Sci, 1997, vol. 94, p. 3789-3794.
Buchholz, et al. Improved properties of FLP recombinase evolved by cyling mutagenesis. Nature Biotechnology, Jul. 1998, vol. 16, p. 657-662.
Supplemental material of Irion. Nature Biotechnology, 2007, vol. 25, No. 12.
Nolden, et al. Site-specific recombination in human embryonic stem cells induced by cell-permeant Cre recombinase. Nature Methods, Jun. 2006, vol. 3, No. 6, p. 461-467.
Berneman, et al. Efficient Non-Viral Transfection of Mouse and Human Embryonic Stem Cells. Blood, Nov. 2004, vol. 104, No. 11, Part 2, p. 402B.
Tan, et al. Comparative Analysis of Sequence-Specific DNA Recombination Systems in Human Embryonic Stem Cells. Stem Cells, 2005, vol. 23, p. 868-873.
Davis, et al. Targeting of the homebox gene, mix11, by homologous recombination in human embryonic stem cells. Mechanisms of Development, Sep. 2005, vol. 122, No. Suppl. 1, p. S170.
Zwaka et al. Homologous recombination in human embryonic stem cells. Nature Biotechnology, Mar. 2003, vol. 21, p. 319-321.
Soriano. Generalized lacZ expression with the ROSA26 Cre reporter strain. Nature Genetics, Jan. 1999, vol. 21, p. 70-71.
Vooijs, et al. A highly efficient ligand-regulated Cre recombinase mouse line shows that LoxP recombination is position dependent. CMBO Reports, 2001, vol. 2, No. 4, p. 292-297.
Mao, et al. Activation of EGFP expression by Cre-mediated excision in a new ROSA26 reporter mouse strain. Blood, Jan. 2001, vol. 97, No. 1, p. 324-326.
Irion, et al. Identification and targeting of the ROSA26 locus in human embryonic stem cells. Nature Biotechnology, Dec. 2007, vol. 25, No. 12, p. 1477-1482.
Oumard et al., "Recommended method for chromosome exploitation: RMCE-based cassette-exchange systems in animal cell biotechnology", Cytotechnology, 2006, vol. 50, p. 93-108.
Dacquin et al., "Mouse α1(I)-Collagen Promoter is the Best Known Promoter to Drive Efficient Cre Recombinase Expression in Osteoblast", Dev. Dynamics, 2002, vol. 224, p. 245-251.
Moses et al., "Embryonic Expression of an Nkx2-5/Cre Gene Using ROSA26 Reporter Mice", Genesis, 2001, vol. 31, p. 176-180.
GenBank CR624523.

* cited by examiner

Fig. 4a

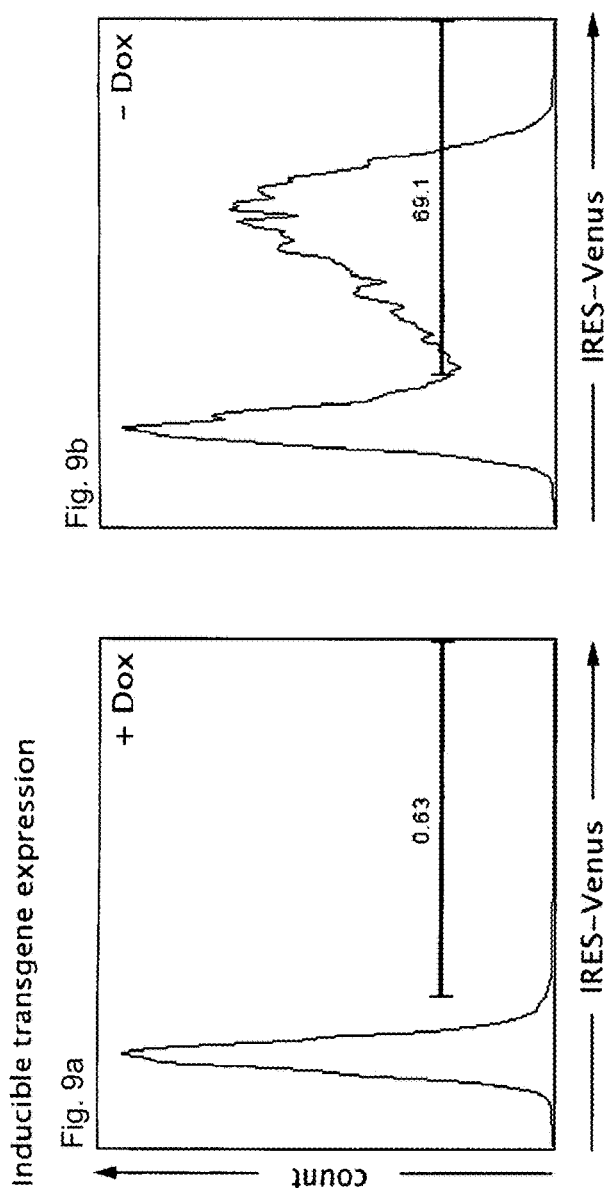

SEQUENCE LISTING

```
<160> NUMBER OF SEQ ID NOS: 20

<210> SEQ ID NO 1
<211> LENGTH: 1072
<212> TYPE: DNA
<213> ORGANISM: Mus sp.

<400> SEQUENCE: 1
tgggccccca cgagcgacca gagttgtcac aaggccgcaa gaacagggga ggtgggggc      60 tcagggacag aaaaaaaagt atgtgtattt tgagagcagg gttgggaggc ctctcctgaa   120
aagggtataa acgtggagta ggcaataccc aggcaaaaag gggagaccag agtaggggga   180
ggggaagagt cctgacccag ggaagacatt aaaaaggtag tggggtcgac tagatgaagg   240
agagcctttc tctctgggca agagcggtgc aatggtgtgt aaaggtagct gagaagacga   300
aaagggcaag catcttcctg ctaccaggct ggggaggccc aggcccacga ccccgaggag   360
agggaacgca gggagactga ggtgacccct ctttccccccg gggcccggtc gtgtggttcg   420
gtgtctcttt tctgttggac ccttaccttg acccaggcgc tgccggggcc tgggcccggg   480
ctgcggcgca cggcactccc gggaggcagc gagactcgag ttaggcccaa cgcggcgcca   540
```

```
cggggtttcc tggccgggaa tggcccgtac ccgtgaggtg ggggtggggg gcagaaaagg      600
cggagcgagc ccgaggcggg gaggggga gg gccaggggcg gaggggggccg gcactactgt    660 gttggcggac tggcgggact agggctgcgt gagtctctga gcgcagcggg cggcggccgc      720
ccctcccccg gcggcggcag cggcggcagc ggcggcagct cactcagccc gctgcccgag      780
cggaaacgcc actgaccgca cggggattcc cagtgccggc gccaggggca cgcgggacac      840
gccccctccc gccgcgccat tggcctctcc gcccaccgcc ccacacttat tggccggtgc      900
gccgccaatc agcggaggct gccggggccg cctaaagaag aggctgtgct ttggggctcc      960
ggctcctcag agagcctcgg ctaggtaggg gatcgggact ctggcgggag ggcggcttgg     1020
tgcgtttgcg gggatgggcg gccgcggcag gccctccgag cgtggtggag cc             1072
```

```
<210> SEQ ID NO 2
<211> LENGTH: 1091
<212> TYPE: DNA
<213> ORGANISM: Homo sapiens

<400> SEQUENCE: 2
```

```
agcgatcaga gttgtctgtc acaaggccgc gagaacgggg gtagggagtg ggggatcggg       60
gagagaaaaa aagtatgcct gtgtatttcg agcggagggc agcaagaggc ctctcctcaa      120
gggaaaggta aacgtggagt aggcagttcc caggaaaggg ggtgaagagg cgttggggga      180
ggggaagcgt cctgacccag gaaaaacatg aaaggggggag ttgggtcgcc tagattagag     240
ggggatctct ctccctggga aaatgggggtg ttgcaacggt gtgtgcaagg cggcgagggg    300
ggtgagaagt ggcagcatcc tcctaagagc ttggggaggg ccaggccac gacccaagga      360 gagcgagcgc ggggagacgg aggaggtgac ccttccctcc cctggggccc gatcgtgagg     420
ttcggtctct tttctgtcgg acccttacct tgtcccagcc gctgccgggg cctgggcccg    480
ggctgcggcg cagggcactc ccgggaggcg gcaggactcg agttaggccc aacgcggcgc    540
cacggcgttt cctggccggg aatggcccgt acccgtgagg tgggggtggg gggcagaaag    600
gcggagcgag ccaaaggcgg ggaggggggg cagggccagg gaaagagggg ggccggcact    660
actgtgttgg cggactggcg ggactggggc tgcgtgagtc tctgagcgca ggcggcggc     720 ggccgcccct cccccggcag cggcggcggc ggcggcggcg gcggcggcgg cggcagctca    780
ctcagcccgc tgcccgagcg gaaacgccac tgaccgcacg ggattccca gcgccggcgc    840 caggggcacc cggacacgc cccctcccgc cgcgccattg gcctctccgc ccaccgcccc    900
gcacccattg gcccactcgc cgccaatcag cggaagccgc cggggccgcc tagagaagag    960
gctgtgcttc ggcgctccgg ctcctcagag agcctcggct aggtagggga gcggaactct   1020
ggtgggaggg gaggtgcggt acactggggg gatgggtggc tagggggggcc gtctggtggc   1080 ttgcggggt t                                                           1091
```

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
tttgaatgat gagccttcgt cccc                                              24
```

```
<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtctcaagt cagtgtacag gtaagc                                         26

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttatccgttg cgtaagcaca gagagg                                         26

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttattctcac ggtgtgcaga ggct                                           24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agaactggaa gtaaacgatt gaaga                                          25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttattctcac ggtgtgcaga ggct                                           24

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgcgtcgac ggctcctcag agagcctcgg ctaggtaggg                          40

<210> SEQ ID NO 10
```

```
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagggttaat taaagatcac gcgaggagga aaggaggg                                38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatggcgcgc ccgtcatcgc ctccatgtcg agtcgctt                                38

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tagcgatatc aaatcagaga cagaaaagtc tttgtcacc                               39

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcgacgagaa gaggctgtgc ttcggcgctc cc                                      32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgagggagc gccgaagcac agcctcttct cg                                      32

<210> SEQ ID NO 15
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ataacttcgt ataatgtatg ctatacgaag ttatgctagc tcatggaacg cgtataactt        60
cgtataaggt atcctatacg aagttatagc t                                       91
```

```
<210> SEQ ID NO 16
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ataacttcgt ataggatacc ttatacgaag ttatacgcgt tccatgagct agcataactt      60
cgtatagcat acattatacg aagttatgta c                                    91

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagaagaggc tgtgcttcgg                                                 20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagaccgcga agagtttgtc c                                               21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccaagaag tgagacaagc                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gacaaggtaa gggtccgaca                                                 20
```

VECTOR FOR TARGETING THE HUMAN ROSA26 GENE

CROSS REFERENCE TO RELATED APPLICATION

This application is a continuation of U.S. patent application Ser. No. 15/331,299 filed Oct. 21, 2016, which is a divisional of U.S. patent application Ser. No. 14/717,472 filed May 20, 2015, which is a continuation of U.S. patent application Ser. No. 12/523,632 filed Sep. 29, 2009, which is a national stage entry under 35 U.S.C. § 371 of International Patent Application No. PCT/US2008/000666 filed Jan. 18, 2008, which claims priority of U.S. Provisional Application No. 60/881,226 filed Jan. 19, 2007, the disclosures of which are incorporated herein by reference in their entireties.

GOVERNMENT SUPPORT

This invention was made with government support under grant numbers HL080627 and GM075019 awarded by the National Institutes of Health. The United States government has certain rights in this invention.

BACKGROUND OF THE INVENTION

The derivation of human embryonic stem cells (hESCs) has opened new avenues for studies on human development and it also provides a potential source of cells for replacement therapy. For example, the ability to genetically alter hESCs offers unique opportunities to study the mechanisms regulating lineage commitment during human development, establish new approaches to identify and screen drugs, and develop in vitro models of human disease. The feasibility of this approach is dependent on the identification of a locus in the genome that is easy to access through targeting and one that will be permissive to expression of the introduced genetic material in the undifferentiated ES cells as well as in a broad range of differentiated cell types generated from these cells. A general review of this approach is provided in Yates et al., Gene Therapy (2006) vol. 13: 1431-1439.

Previous studies aimed at expressing genes in hESCs and derivative lineages have used either lentiviral vectors or transgenes that integrate randomly into the genome. These approaches are problematic for a number of reasons, e.g., a randomly integrated vector can activate or suppress expression of endogenous genes through insertional mutagenesis, the vectors are often present in multiple copies, and their expression is subject to silencing.

Homologous recombination in mouse embryonic stem cells has been used to produce mice carrying a single copy of the transgene integrated into a predetermined site of the genome (see e.g., Shaw-White et al., Transgenic Res.; (1):1-13 (1993); Bronson et al., Proc. Natl. Acad. Sci. USA, 93(17:9067-72 (1996); Hatada et al., J. Biol., Chem., 274 (2):948-55 (1999); Tang et al., Genesis, 32(3):199-202 (2002)). In these studies, the ubiquitous Hprt locus was used with limited and unpredictable success. It would be desirable to define an autosomal locus that allows strong and predictable expression of transgenes inserted through homologous recombination, but is difficult to identify chromosomal loci that fulfill these criteria. Exogenous transgenes may not harbor all of the sequences necessary and sufficient for proper regulation of transcription and may therefore be influenced by cis-regulatory elements near the site of insertion.

In the mouse, a locus known as Rosa26 locus meets these criteria because it is expressed in ES cells and many derivative tissues both in vitro and in vivo and new genetic material can be easily introduced into it through homologous recombination. WO 99/53017 describes a process for making transgenic animals that ubiquitously express a heterologous gene, wherein the heterologous gene is under the control of a ubiquitously expressed endogenous promoter, e.g., that of the mouse Rosa26 locus. R. Dacquin et al., Dev. Dynamics 224:245-251 (2002) and K. A. Moses et al., Genesis 31:176-180 (2001) utilize the transgenic mouse strain R26R obtained according to WO 99/53017 for the expression of heterologous genes. WO 02/098217 describes a method of targeting promoter-less selection cassettes into transcriptionally active loci, such as the Rosa26 locus. WO 03/020743 describes the expression of transgenes in vivo by targeting protected transgene cassettes into predetermined loci (e.g. the Rosa26 locus), such that the introduced tissue specific exogenous promoter has at least some tissue specific activity.

US 2006/0205077 describes a method for targeted transgenesis using the mRosa26 locus. U.S. Pat. No. 6,461,864 also describes the use of the mRosa26 locus in the production of genetically engineered non-human animals that express a heterologous DNA segment.

SUMMARY OF THE INVENTION

The present invention is based on the identification of the human Rosa26 (hRosa26) locus, which is capable of preserving the activity of heterologous promoters inserted through homologous recombination at the locus. Human Rosa26 is therefore useful for the efficient generation of transgenic animals, tissues and cell populations with a predictable transgene expression pattern.

Therefore, the present invention provides a method for generating a transgenic eukaryotic cell population having a modified human Rosa26 locus, which method comprises introducing a functional DNA sequence into the human Rosa26 locus of starting eukaryotic cells. In one embodiment, the functional DNA sequence is a gene expression cassette comprising a gene of interest operatively linked to a heterologous promoter; alternatively, the functional DNA sequence is a gene expression cassette comprising a gene of interest, wherein the DNA sequence becomes integrated into the locus by homologous recombination, thereby inserting the DNA sequence into the locus such that expression of the DNA sequence is under the control of the endogenous hRosa26 promoter.

In the method of the present invention, the functional DNA sequence is introduced into the eukaryotic cells by homologous recombination with a targeting vector comprising the functional DNA sequence flanked by DNA sequences homologous to the human Rosa26 locus. The eukaryotic cells are selected from the group consisting of primary cells and immortalized cells, and in a particular embodiment the eukaryotic cells are human embryonic stem (ES) cells.

The gene of interest may be any DNA sequence. A non-limiting list of genes that may be used in the method of the present invention includes recombinases, reporter genes, receptors, signaling molecules, transcription factors, pharmaceutically active proteins and peptides, drug target candidates, disease causing gene products and toxins, and mutations and combinations thereof.

In one embodiment, the functional DNA sequence is a gene expression cassette comprising a gene of interest operatively linked to a heterologous promoter, wherein the promoter is selected from the group consisting of a constitutive ubiquitous promoter, a constitutive tissue specific promoter, an inducible ubiquitous promoter and an inducible tissue specific promoter. A non-limiting list of suitable promoters includes CAGGS, hCMV, PGK, FABP, Lck, CamKII, CD19, Keratin, Albumin, aP2, Insulin, MCK, MyHC, WAP, Col2A, Mx, tet and Trex promoter.

The functional DNA sequence or gene expression cassette used in the method of the present invention further comprises one or more additional functional sequences selected from the group consisting of marker genes, one or more recombinase recognition sites which may be the same or different, poly A signal, introns, and combinations thereof. For example, the expression cassette comprises one or more functional sequences selected from the group consisting of a viral splice acceptor, a loxP-flanked promoterless neomycin resistance gene, an inverted RFP variant, mutant loxP2272 sites, and combinations thereof. In a particular embodiment, the expression cassette comprises the following elements in sequential order: (a) a viral splice acceptor, (b) a loxP-flanked promoterless neomycin resistance gene, and (c) an inverted RFP variant (tdRFP), wherein said inverted RFP variant is flanked by mutant loxP2272 sites. Specifically, the expression cassette comprises a DNA sequence coding for a Cre recombinase and said loxP and mutant loxP2272 sites are positioned such that following expression of Cre recombinase, the neomycin resistance cassette is removed and the tdRFP inverted, placing it under control of the endogenous hROSA26 promoter.

Still further, the targeting vector used in the invention further comprises functional sequences selected from the group consisting of tags for protein detection, enhancers, selection markers, and combinations thereof.

The transgenic eukaryotic cells are derived from human and the DNA sequences homologous to the human Rosa26 locus are derived from the 5' and 3' flanking arm of the human Rosa26 locus. In one embodiment, the targeting vector comprises a functional DNA sequence flanked by DNA sequence homologous with a human Rosa26 locus.

The invention also comprises a eukaryotic cell population comprising a modified human Rosa26 locus.

The invention additionally provides an isolated DNA sequence substantially homologous to a nucleotide sequence located between nucleotide positions 9'415'082 and 9'414'043 on chromosome 3. Alternatively, the invention provides an isolated DNA sequence substantially homologous to SEQ ID NO:2. Still further, the invention provides an isolated DNA sequence that hybridizes under stringent conditions to the nucleic acid sequence of SEQ ID NO:2.

Also provided is a transgenic non-human animal comprising a modified human Rosa26 locus.

BRIEF DESCRIPTION OF THE DRAWINGS

FIG. 1a shows the expression of hRosa26 in different adult tissues and in 3 hESC lines (HI, HES2, HES3). Expression of ExonIII was detected using quantitative PCR. Data is represented as the average expression from 2 to 4 individual RT/qPCR reactions. FIG. 1b shows the expression of ExonII and ExonIII evaluated using RT-PCR; +/−RT indicates the presence of absence of reverse transcriptase. This PCR amplifies a 260 bp product spanning the putative intron. FIG. 1c is a schematic representation of the targeting vector and a segment of the newly identified human Rosa26 locus. Grey triangles denote wild-type loxP and white triangles mutant loxP2272 sites (SA=splice acceptor). The box with vertical bars indicates the region of highest sequence homology (>85%) between mouse and human. Putative exons 1 and 2 were mapped according to the positions of electronically identified ESTs/transcripts. FIG. 1d shows the human Rosa26 locus after gene targeting and cremediated activation of tdRFP. FIG. 1e is a Southern blot of parental HES2 and targeted hRosa26 cell lines before (WT/KI) and after Cre mediated tdRFP inversion (WT/KI tdRFP). WT=wild type, KI=knock-in. FIG. 1f shows hRosa26 genomic DNA hybridized with a tdRFP specific probe identifying a single integration event.

FIG. 2a shows the morphology of the targeted hRosa26 ES cells grown on mouse embryonic feeder cells using light microscopy. FIG. 2b shows the expression of tdRFP in hRosa26 ES cells revealed by fluorescence microscopy. FIG. 2c shows the alkaline phosphatase expression in the targeted in hRosa26 ES cells grown on Matrigel for 4 passages. FIG. 2d shows five-day-old EBs derived from hRosa26 ES cells; phase contrast. FIG. 2e shows the expression of tdRFP in hRosa26 EBs revealed by fluorescence microscopy and FIG. 2f shows the flow cytometric analysis of the targeted hRosa26 cells (shaded and without hatching), the parental HES2 cells (hatched and shaded) and cells from day 17 hRosa26 EBs (bold line). Teratoma derived from hRosa26 ES cells shown under bright (FIG. 2g) and epifluorescent light (FIG. 2h). The inserts show single cells from a different hRosa26 subclone (phase contrast and fluorescence microscopy, FIG. 2g and FIG. 2h, respectively). FIG. 2i shows the flow cytometric analysis showing tdRFP expression in a large majority (>96%) of the teratoma cells. Live cells (>60%) were gated based on forward and side scatter parameters.

FIG. 3a shows developing neurons expressing β-Tubulin III (green) and tdRFP (red). Total population is visualized by nuclear DAPI staining (blue). Insert: overlay demonstrating co-expression of tdRFP and β-Tubulin III. FIG. 3b shows tdRFP expression in AFP cells generated from hRosa26 (upper panel) and wild type (HES2) cells (lower panel). The first column represents an overlay of an IgG control (green), tdRFP and DAPI. The second, third and fourth column show individual channels for AFP staining (green), tdRFP (red) and DAPI (blue), respectively. FIG. 3c shows myeloid (M) and erythroid (E) hematopoietic colonies grown from day 18 EBs generated from the hRosa26 cells. The insert shows tdRFP expression in both types of colonies. Exposure with the GFP filter is included to control for auto fluorescence (EGFP). FIG. 3d shows flow cytometric analysis demonstrating CD45 and tdRFP expression at days 14 and 21 in EB-derived cells generated from hRosa26 hESCs (red) or wild type hESCs (blue). FIG. 3e shows the expression of tdRFP in human chorionic gonadotropin positive cells generated from hRosa26 cells (left, center left and center right) and HES2 parental cells (right). The hESC were differentiated in serum free media with high concentrations of human BMP4 (100 ng/ml) to induce trophectoderm differentiation. After 14 days cells were stained with an antibody specific for human chorionic gonadotropin subunit B (hCG) or an isotype control (center right, IgG).

Figure 4A:
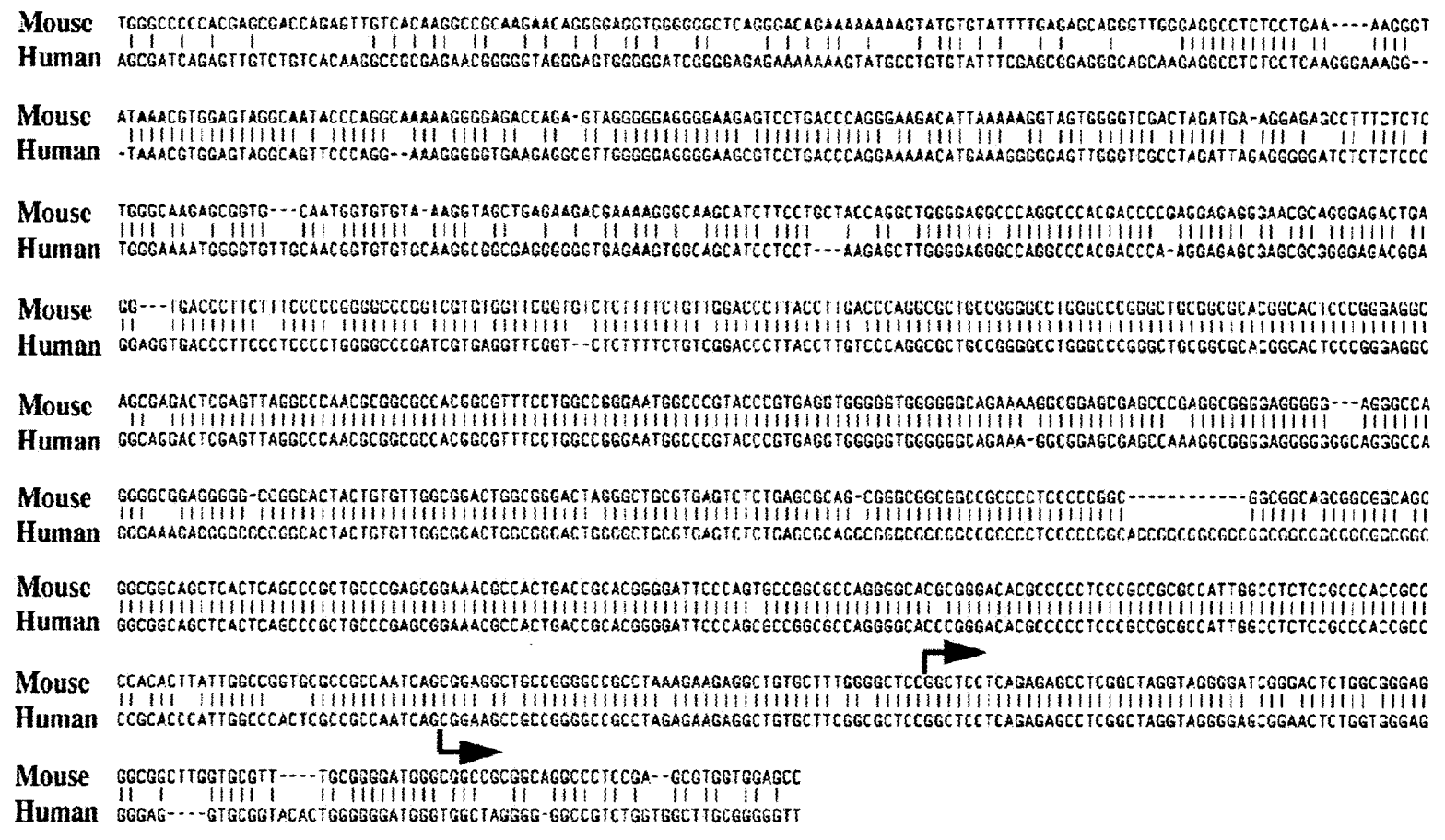

FIG. 4a and FIG. 4b show the alignment of the mouse and human Rosa26 sequences and multiple alignment plot of selected human ESTs. FIG. 4a shows the alignment of the mouse and human Rosa26 sequences with the highest degree of homology (>85%; box with vertical bars in FIG. 1c; the mouse sequence depicted in FIG. 4a is SEQ ID NO: 1 and the human sequence depicted in FIG. 4a is SEQ ID NO: 2). The top arrow denotes the 5' start of the mouse Rosa26 transcript 1, the bottom arrow indicates the start of the most 5' human transcript found in Ensembl database (GenBank: CR624523). The human sequence shown is located between nucleotide positions 9'415'082 and 9'414'043 on chromosome 3 (Ensembl Human Blast View v37). FIG. 4b shows the multiple alignment plot of selected human ESTs showing local similarities to the genomic sequence of the putative hRosa26 locus. Areas of significant similarities (>60%) are boxed. Each EST is labeled with its GenBank accession number and the tissue source. Predicted exons are indicated as black bars on a genomic DNA representation and numbered using Roman numerals. In the mouse, Rosa26 overlaps with the ThumpD3 gene which is positioned in the reverse orientation downstream of the Rosa26 transcription unit. To highlight the high degree of synteny between this human chromosomal region and the mouse Rosa26 locus, exon structure of the human THUMPD3 is also represented as gray bars.

FIG. 5a is a schematic drawing of the hRosa26 locus after Cre mediated tdRFP activation. EcoR1=EcoR1 restriction enzyme, ProbeRFP=1.4 kb tdRFP internal Southern blot probe. FIG. 5b shows hRosa26 genomic DNA was digested with EcoRI and hybridized with a tdRFP specific probe (same gel as in FIG. 1f). 1 kb=1 kb plus DNA ladder (Invitrogen), EtBr=ethidium bromide.

FIG. 6a shows hRosa26.2 and control genomic DNA were digested with HindIII and hybridized with a 900 bp external genomic probe revealing the 6 kb wild-type (WT) and 3.5 kb knock-in (KI) allele. FIG. 6b shows hRosa26.2 and HES2 parental cells were differentiated under serum free conditions to mesoderm and hematopoietic cells. After 17 days of differentiation EB-derived cells were analyzed for the expression of tdRFP and CD45.

FIG. 7a. cartilage (*). FIG. 7b. striated cardiac muscle with centrally located nuclei (arrow). FIG. 7c. ciliated mucosal tissue (*) with secretory Goblet cells (arrow). FIG. 7d. neural rosettes (arrow).

FIG. 8a is a schematic representation of the hRosa26 genomic locus before targeting; FIG. 8b shows the locus after targeting and Cre mediated tdRFP inversion; and FIG. 8c shows the locus following exchange of the tdRFP to puroTK with RMCE. Filled triangles denotes the wild-type loxP site and the open triangles the mutant loxP2272 site. SA=splice acceptor. FIG. 8d is a Southern blot of genomic DNA (digested with XbaI) hybridized with a puro specific probe revealing a single integration at 6.1 kb. FIG. 8e is a southern blot analysis of hRosa26 clones before and after RMCE. Genomic DNA was digested with HindIII and subsequently hybridized with a hRosa26 external probe (same probe as in FIG. 1e).

FIG. 9a and FIG. 9b show inducible expression from the human Rosa26 locus. Using RMCE, an inducible expression cassette was introduced into the human Rosa26 locus. This vector contains both the tetracycline-controlled transactivator as well as a tetracycline response element. In addition a transgene can be introduced and is expressed upon the removal of doxycycline. Expression of the transgene can be monitored by the expression of the Venus fluorescent protein expressed from an internal ribosomal entry site (IRES). As shown in FIG. 9a, in the presence of doxycycline (+Dox) no Venus protein can be detected by flow cytometry, however upon removal of dox high levels of the fluorescent reporter can be detected (FIG. 9b).

DETAILED DESCRIPTION OF THE INVENTION

Figure 1A:
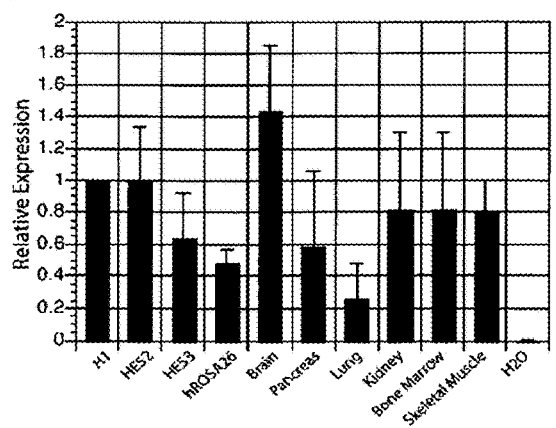
FIG. 1a, FIG. 1b, FIG. 1c, FIG. 1d, FIG. 1e and FIG. 1f show the identification, expression and targeting of the hRosa26 locus.

The present invention provides the human homologue of the mouse Rosa26 locus and methods for site-specific integration of a transgene into the human Rosa26 locus. Therefore, the invention provides an isolated DNA sequence substantially homologous to a nucleotide sequence located between nucleotide positions 9'415'082 and 9'414'043 on chromosome 3. The invention further provides an isolated DNA sequence substantially homologous to SEQ ID NO: 2. And also provided is an isolated DNA sequence that hybridizes under stringent conditions to the nucleic acid sequence of SEQ ID NO:2.

The terms "substantially homologous", "substantially corresponds to", and "substantial identity" as used herein denotes a characteristic of a nucleic acid sequence such that a nucleic acid sequence has at least about 90% sequence identity, and most preferably at least about 95% sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long.

"Substantially complementary" as used herein refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogenic DNA homology clamps, although it is recognized that the presence of various recombinases may reduce the degree of sequence identity required for efficient recombination.

"Stringent conditions" refer to conditions under which a specific hybrid is formed. Generally, stringent conditions include conditions under which nucleic acid molecules having high homology, for example, preferably 90% or most preferably 95%, hybridize with each other. Alternatively, stringent conditions generally include conditions whereby nucleic acid molecules hybridize with each other at a salt concentration corresponding to a typical washing condition of Southern hybridization, i.e., approximately 1×SSC, 0.1% SDS, preferably 0.1×SSC, 0.1% SDS, at 60° C.

Any method known in the art may be used for the site-specific integration of a transgene using the human Rosa26 locus. Suitable, but non-limiting examples of various methods that may be used in connection with the hRosa26 locus are described in Yates et al., *Gene Therapy* (2006) vol. 13: 1431-1439; Shaw-White et al., Transgenic Res.; (1):1-13 (1993); Bronson et al., Proc. Natl. Acad. Sci. USA, 93(17:9067-72 (1996); Hatada et al., J. Biol., Chem., 274(2):948-55 (1999); Tang et al., Genesis, 32(3):199-202 (2002); WO 99/53017; R. Dacquin et al., Dev. Dynamics 224:245-251 (2002); K. A. Moses et al., Genesis 31:176-180 (2001); WO 03/020743; US 2006/0205077; and U.S. Pat. No. 6,461,864; the disclosures of which are incorporated herein by reference in their entirety.

For example, a targeting vector may be engineered for the site-specific integration of a transgene using the hRosa26 locus by methods known in the art. A targeting vector generally comprises a first sequence homologous to a portion or a region of a target gene sequence, i.e., the hRosa26 locus, and a second sequence homologous to a second portion or region of a target gene sequence, i.e., a second portion of the hRosa26 locus. The targeting vector may also include a selectable marker cassette that comprises a selectable marker gene. Preferably, the selectable marker cassette is positioned in between the first and the second sequence homologous to a region or portion of the target gene sequence. The selectable marker cassette may further comprise a sequence that initiates, directs, or mediates transcription of the selectable marker and the targeting vector also comprises a regulator that has the ability to control or regulate the expression of the selectable marker.

In one embodiment of the invention, the functional DNA sequence introduced into the hRosa26 locus is a gene expression cassette comprising a gene of interest operatively linked to a heterologous promoter. As used herein, the term "promoter", generally refers to a regulatory region of DNA capable of initiating, directing and mediating the transcription of a nucleic acid sequence. Promoters may additionally comprise recognition sequences, such as upstream or downstream promoter or enhancer elements, which may influence the transcription rate.

In one embodiment of the present invention, a promoter may be used in the gene expression cassette (which is a heterologous promoter relative to the hRosa26 locus) that is a ubiquitous or tissue specific promoter, either constitutive or inducible. This ubiquitous promoter is selected from polymerases I, II and III dependent promoters, preferably is a polymerase II or III dependent promoter including, but not limited to, a CMV promoter, a CAGGS promoter, a snRNA promoter such as U6, a RNAse P RNA promoter such as H1, a tRNA promoter, a 7SL RNA promoter, a 5 S rRNA promoter, etc. Suitable examples of ubiquitous promoters are CAGGS, hCMV, PGK, and examples of tissue specific promoters are FABP (Saam & Gordon, J. Biol. Chem., 274:38071-38082 (1999)), Lck (Orban et al., Proc. Natl. Acad. Sci. USA, 89:6861-5 (1992)), CamKII (Tsien et al., Cell 87: 1317-1326 (1996)), CD19 (Rickert et al., Nucleic Acids Res. 25:1317-1318 (1997)); Keratin (Li et al., Development, 128:675-88 (201)), Albumin (Postic & Magnuson, Genesis, 26:149-150 (2000)), aP2 (Barlow et al., Nucleic Acids Res., 25 (1997)), Insulin (Ray et al., Int. J. Pancreatol. 25:157-63 (1999)), MCK (Bruning et al., Molecular Cell 2:559-569 (1998)), MyHC (Agak et al., J. Clin. Invest., 100:169-179 (1997), WAP (Utomo et al., Nat. Biotechnol. 17:1091-1096 (1999)), Col2A (Ovchinnikov et al., Genesis, 26:145-146 (2000)); examples of inducible promoter sites are Mx (Kuhn et al. Scinence, 269: 1427-1429 (1995)), tet (Urlinger et al., Proc. Natl. Acad. Sci. USA, 97:7963-8 (2000)), Trex (Feng and Erikson, Human Gene Therapy, 10:419-27). Suitable inducible promoters are the above-mentioned promoters containing an operator sequence including, but not limited to, tet, Ga14, lac, etc.

Alternatively, as described hereinabove, the expression cassette may comprise a gene of interest and other integration elements such that when the DNA sequence is integrated into the locus by homologous recombination, expression of the DNA sequence is under control of the endogenous hRosa26 promoter. For example, the expression cassette may include a sequence flanked by a recombinase recognition site, e.g., loxP, and the cassette is engineered such that following expression of the recombinase, the functional DNA sequence is placed under the control of the endogenous hRosa26 promoter. In particular, the expression cassette may include a viral splice acceptor, followed by a loxP-flanked promoterless neomycin resistance gene, which is followed by an inverted RFP variant (a tandem-dimer RFP or tdRFP), flanked by mutant loxP2272 sites. As described above, the loxP and loxP2272 sites are positioned such that after Cre expression, the neomycin resistance cassette is removed and the tdRFP is inverted, thereby placing the cassette under the control of the endogenous hRosa26 promoter.

The targeting vector, functional DNA sequence or gene expression cassette may further comprise one or more additional sequences including but not limited to (selectable) marker genes (such as the neomycin phosphotransferase gene of E. coli transposon, etc.), recombinase recognition sites (which include loxP, FRT, variants thereof, etc.), poly A signals (such as synthetic polyadenylation sites, or the polyadenylation site of human growth hormones, etc.), splice acceptor sequences (such as a splice acceptor of adenovirus, etc.), introns, tags for protein detection, enhancers, selection markers, etc.

In a preferred embodiment, the targeting vector comprises a functional DNA sequence flanked by DNA sequences homologous to the human Rosa26 locus. Although the size of each flanking region is not critical and can range from as few as 100 base pairs to as many as 100 kb, preferably each flanking fragment is greater than about 1 kb in length, more preferably between about 1 and about 10 kb, and even more preferably between about 1 and about 5 kb. Although larger fragments may increase the number of homologous recombination events in ES cells, larger fragments will also be more difficult to clone.

In another embodiment, the method of the invention includes homologous recombination and the expression cassette is free of a transcriptional stop signal 5' to the (heterologous) promoter of the cassette (i.e. is a non-protected cassette); and/or the exogenous promoter is a ubiquitous (constitutive or inducible) promoter.

The hRosa26 locus may be used for the site-specific integration of a transgene, wherein the transgene includes a gene of interest. As used herein, a transgene includes a gene or any DNA sequence that has been introduced into a targeting vector and ultimately into a different cell population or organism. This non-native segment of DNA may retain its original biological properties and functions, e.g., to produce RNA or protein, once transferred or introduced into the transgenic organism, or it may alter the normal function of the transgenic organism's genetic code.

The gene of interest includes any gene or DNA sequence of natural or synthetic origin. A non-limiting list of genes that may be used in the method of the present invention is selected from the group of genes consisting of recombinases, reporter genes, receptors, signaling molecules, transcription factors, pharmaceutically active proteins and peptides, drug target candidates, disease causing gene products and toxins, and mutations and combinations thereof. The term "mutation" is understood to mean any changes introduced into the DNA sequence of a reference gene.

In one embodiment, the ES cell is a human ES cell. ES cells may be obtained commercially or isolated from blastocysts by methods known in the art, as described for example by U.S. Pat. No. 5,843,780; Thompson et al. (1998) Science 282:1145-1147; U.S. Pat. No. 6,492,575; Evans et al. (1981) Nature 292:154-156; and Reubinoff et al. (2000) Nature Biotech. 18:399. The method described herein may also be used to deliver a transgene to an adult, i.e. somatic, stem cell. Adult stem cells include, for example, hematopoietic stem cells, bone marrow stromal stem cells, adipose derived adult stem cells, olfactory adult stem cells, neuronal stem cells, skin stem cells, and so on. Adult stem cells have a similar ability as ES cells to give rise to many different cell types, but have the advantage that they can be harvested from an adult.

The undifferentiated ES cells are preferably maintained under conditions that allow maintenance of healthy colonies in an undifferentiated state. For example, human ES cells may be maintained on a feeder layer such as irradiated mouse embryonic fibroblasts in the presence of serum, or with serum replacement in the presence of bFGF, or in medium conditioned by mouse embryonic fibroblasts, or under serum free conditions using human feeder layers derived from, for example, human embryonic fibroblasts, fallopian tube epithelial cells or foreskin.

The method of the present invention results in site-specific integration of the transgene at the hRosa26 locus of the ES cell genome. The ES cells having the integrated transgene undergo normal embryoid body (EB) development and retain the capacity to differentiate into multiple cell types. Expression of the transgene is maintained throughout differentiation. Further, the ES cells having the integrated transgene maintain the capacity to generate cells of multiple lineages.

Stem cells having a transgene integrated therein as made by the method of the present invention are useful, inter alia, for generating transgenic non-human animals, for generating differentiated cells and tissues having a transgene integrated therein, for studying differentiation of stem cells, for evaluating strategies for safe and effective gene targeting in stem cells, and for targeted therapeutic gene transfer. Methods for generating differentiated cells from stem cells are known in the art. The model system for ES cell in vitro differentiation is based on the formation of three dimensional structures known as embryoid bodies (EBs) that contain developing cell populations presenting derivatives of all three germ layers and is disclosed in the art, for example by Keller (1995) Curr. Opin. Cell Biol. 7:862-869.

For example in one embodiment, prior to differentiation, ES cells are removed from feeder cells prior to differentiation by subcloning the ES cells directly onto a gelatinized culture vessel. Twenty-four to 48 hours prior to the initiation of EB generation, ES cells are passaged into IMDM-ES. Following 1-2 days culture in this medium, cells are harvested and transferred into liquid medium (IMDM, 15% FBS, glutamine, transferrin, ascorbic acid, monothioglycerol and protein free hybridoma medium II) in Petri-grade dishes. Under these conditions, ES cells are unable to adhere to the surface of the culture dish, and will generate EBs.

Culture conditions are known in the art for the differentiation to cell types found in blood (Wiles et al. (1991) Development 111:259-67), heart (Maltsev et al. (1993) Mech. Dev. 44:41-50), muscle (Rohwedel et al. (1994) Dev. Biol. 164:87-101), blood vessels (Yamashita et al. (2000) Nature 408:92-96), brain (Bain et al. (1995) Dev. Biol. 168:342), bone (Buttery et al. (2001) Tissue Eng. 7:89-99) and reproductive system (Toyooka et al. (2003) Proc. Natl. Acad. Sci. USA 100:11457-11462).

The differentiated cells and/or tissue generated therefrom may be introduced in an animal for therapeutic purposes. Accordingly, in another embodiment the present invention provides an animal comprising differentiated cells having a transgene integrated into the hRosa26 locus thereof, or comprising a tissue generated from such cells. In one embodiment the differentiated cell is a hemotopoietic cell, endothelial cell, cardiomyocyte, skeletal muscle cell or neuronal cell. The cells or tissues may be transplanted into the animal by methods known in the art.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

EXAMPLES

Materials and Methods:
Human ES Culture:

The human embryonic stem cell line HES 2 (ES Cell International) was grown on irradiated Swiss Webster or DR4 mouse embryonic feeder cells (MEF, The Jackson Laboratory) in DMEM/F12 supplemented with 20% (v/v) knockout serum replacement, 5% (v/v) MEF conditioned medium, bFGF (5 to 20 ng/mL, R&D Systems), 50 U/mL penicillin, 50 µg/mL streptomycin (P/S), 2 mM L-glutamine (Glut), 0.1 mM non essential amino acids (all from Invitrogen), 0.1 mM ßmercapto-ethanol (ß-ME)29. MEF cells were generated and cultured as described in. Kennedy, M. & Keller, G. M. Hematopoietic commitment of ES cells in culture. Methods Enzymol 365, 39-59 (2003).

hRosa26 Morphology:

hRosa26 hESCs were grown on either MEF cells or Matrigel (Becton Dickinson). Alkaline phosphatase staining was performed as described by the manufacturer (Vector-Labs). tdRFP expression was detected using a LEICA DM IRB inverted microscope.

Identification of Putative Transcripts from the Human Rosa26 Locus:

To isolate human ESTs showing similarities to the human Rosa26 locus, putative exons were identified by comparing published mouse Rosa26 transcripts to the human ROSA26 genomic sequence. Each individual exon was then blasted against the whole human EST database using BlastN (NCBI). ESTs showing a significant E value (E>0,0001) were globally aligned against the putative human Rosa26 genomic sequence using the Align Plus 5 software from Scientific & Educational Software (Penalties for Mismatch: 2, Gap Opening: 4, Gap Extension: 1). For analysis by quantitative PCR (qPCR) and RT-PCR total RNA from brain, pancreas, lung, kidney, bone marrow and skeletal muscle was purchased from Clontech, or isolated from HES cell lines H1 (WiCell), HES2, HES3 (both ES Cell International) and hRosa26 using the RNeasy kit (Qiagen). Reverse transcription was used to generate cDNA (Omniscript RT, Qiagen).

Human β-ACTIN cDNA was detected using the following primers: fwd 5' TTT GAA TGA TGA GCC TTC GTC CCC 3' (SEQ ID NO: 3) and rv 5' GGT CTC AAG TCA GTG TAC AGG TAA GC 3' (SEQ ID NO: 4). hRosa26 ExonIII cDNA was detected by qPCR using the following primer set: fwd 5' TTA TCC GTT GCG TAA GCA CAG AGA GG 3' (SEQ ID NO: 5) and rv 5' TTA TTC TCA CGG TGT GCA GAG GCT 3' (SEQ ID NO: 6). ExonII and ExonIII cDNA by RT-PCR was detected using the following primer set: fwd 5' AGA ACT GGA AGT AAA CGA TTG AAG A 3' (SEQ ID NO: 7) and rv 5' TTA TTC TCA CGG TGT GCA GAG GCT 3' (SEQ ID NO: 8). For qPCR analysis samples were analyzed on an ABI 7900HT thermocycler and amplification was detected using the SYBR green method (BioRad, iQ SYBR green supermix). Linearity of amplification was tested on genomic DNA samples. The amount of target, normalized to the β-ACTIN reference and relative to the H1 hESC line was calculated by: 2-ΔΔCT. The resulting qPCR product was confirmed by sequencing and showed hRosa26 sequence.

Vector Design:

The targeting vector was constructed using the backbone of pHL-HH, a murine Rosa26 targeting vector8. It consisted of 5' and 3' arms of homology, a loxP/loxP2272 flanked neomycin resistance cassette, an inverted loxP/loxP2272 flanked tdRFP and a diphtheria toxin negative selection cassette. The homology arms were amplified by long range genomic PCR from hESC line HES2 using PCR primers introducing the restriction sites indicated: short arm fwd 5' ATG CGT CGA CGG CTC CTC AGA GAG CCT CGG CTA GGT AGG G 3' (SalI) (SEQ ID NO: 9) and rv 5' TAG GGT TAA TTA AAG ATC ACG CGA GGA GGA AAG GAG GG 3' (PacI) (SEQ ID NO: 10), long arm fwd 5' TAT GGC GCG CCC GTC ATC GCC TCC ATG TCG AGT CGC TT 3' (AscI) (SEQ ID NO: 11) and rv 5' TAG CGA TAT CAA ATC AGA GAC AGA AAA GTC TTT GTC ACC 3' (EcoRV) (SEQ ID NO: 12). Subsequently the murine SA and LA in the plasmid pHL-HH were exchanged to the human counterpart. A mock screening plasmid was generated with an extended 5' homoly arm which was introduced as a linker using the following oligonucleotides: fwd 5' TCG ACG AGA AGA GGC TGT GCT TCG GCG CTC CC 3' (SEQ ID NO: 13) and rv 5' TCG AGG GAG CGC CGA AGC ACA GCC TCT TCT CG 3' (SEQ ID NO: 14). The RMCE exchange vector was created by ligating an oligonucleotide linker harboring a loxP and mutant loxP2272 site as well as multiple cloning site (MCS) into the SacI/KpnI sites of plasmid pBluescript II SK+ (Stratagene). Linker sequence is as follows: fwd 5' ATA ACT TCG TAT AAT GTA TGC TAT ACG AAG TTA TGC TAG CTC ATG AAA CGC GTA TAA CTT CGT ATA AGG TAT CCT ATA CGA AGT TAT AGC T 3' (SEQ ID NO: 15) and rv 5' ATA ACT TCG TAT AGG ATA CCT TAT ACG AAG TTA TAC GCG TTT CAT GAG CTA GCA TAA CTT CGT ATA GCA TAC ATT ATA CGA AGT TAT GTA C 3' (SEQ ID NO: 16). The puromycin-thymidine-kinase (puroTK) cassette from pBSKpuroTK was introduced into the MCS using standard molecular techniques.

Plasmid Preparation and Electroporation:

Forty µg of the targeting plasmid was linearized using KpnI restriction enzyme (NEB). One day prior to electroporation DR4 feeder cells were plated on 10 cm tissue culture treated dishes coated with a thin layer of Matrigel. For DNA electroporation human ES cells (passage 16) were collected by trypsinization and dissociated into single cells by trituration. Trypsin activity was inhibited using 50% (v/v) fetal calf serum (Atlas). 5×106 cells were electroporated using a BioRad gene pulser (BioRad, 250V/500 µFd14 in 500 µL HES media +300 µL Phosphate Buffered Saline (PBS) containing the linearized targeting plasmid. Following electroporation the cells were plated on DR4 MEF cells at 2.5×106 cells/10 ml. Twenty-four hours later G418 (Invitrogen) was added to the culture at 25 µg/mL. The concentration of G418 was increased to 50 µg/mL at day 4 of culture. Media was changed every one to two days. The resulting colonies were screened on day 12 for correct targeting of the locus by polymerase chain reaction (PCR) using the following primer set: fwd 5' GAG AAG AGG CTG TGC TTC GG 3' (SEQ ID NO: 17) and rv 5' AAG ACC GCG AAG AGT TTG TCC 3' (SEQ ID NO: 18) amplifying a 1.3 kb fragment.

Transient Cre Expression and Cell Sorting:

hRosa26 clone B7 was expanded and electroporated with a Cre expressing plasmid (pCRE-AC, HJF, unpublished). Following electroporation cells were plated on Matrigel coated plates in HES medium. Forty-eight hours after electroporation cells were harvested using trypsin-EDTA and resuspended in cell sorting media (IMDM+10% FCS) and sorted based on the expression of tdRFP. Two thousand tdRFP+ sorted cells were plated on embryonic feeder cells in hESC media. Individual tdRFP+ clones were identified, picked using a glass pipette and expanded.

Southern Blot Analysis:

hRosa26 targeting was confirmed by Southern blot analysis using a 5' external probe amplified from genomic DNA using the following primer pair: fwd 5' GCC CAA GAA GTG AGA CAA GC 3' (SEQ ID NO: 19), rv 5' GAC AAG GTA AGG GTC CGA CA 3' (SEQ ID NO: 20), generating a 900 bp probe. Genomic DNA was digested using the HindIII restriction enzyme. Expected band sizes are 6 kb for the wild type allele and 3.5 kb for the targeted allele. For the internal probe a 1.4 kb tdRFP probe derived from the targeting vector was used that would detect one 4.1 kb band (EcoR1 digest), if a single integration event has occurred. For RMCE Southern blot analysis using an internal probe genomic DNA was digested using the restriction enzyme Xba1 and then hybridized with a 1.6 kb puroTK probe derived from plasmid pBSKpuroTK. This probe will detect one 6.1 kb band if a single copy of the construct was integrated.

ES Differentiation:

For all differentiation experiments hESCs were maintained on irradiated MEF cells in HES media. Prior to the onset of the experiments cells were passaged once on Matrigel coated plates to reduce the number of feeders. All cytokines were purchased from R&D Systems.

Neuroectoderm Differentiation:

Cells were harvested by trypsinization and induced to form EBs by plating at a concentration of 50,000 cells/100 µl in 96-well low cluster plates (Corning) in the following media: 50% (v/v) DMEM-F12, 50% (v/v) Neurobasal media (both from Invitrogen) supplemented with P/S, Glut, 4.5× 10−4 M monothioglycerol (MTG), 0.5 mM ascorbic acid (AA), 0.1% (m/v) albumin (all from Sigma), 0.5×N2 and 0.5×B27 supplement (both from Invitrogen) (SF-ES). At day 4 of differentiation bFGF was added at a concentration of 20 ng/mL. At day 6 cells were transferred to gelatin coated 6 well plates and media was supplemented with epidermal growth factor (EGF, 20 ng/mL). Medium was subsequently changed every 3-5 days using SF-ES medium supplemented with bFGF and EGF. In some experiments cells were grown on glass coverslips, embedded in the gelatin coatin. Cells were analyzed after 21 days in culture. Antibody staining was performed as follows: cells were fixed in PBS+4% Paraformaldehyde (PFA, EMS), blocked with serum free protein block (DAKO) and subsequently stained with monoclonal mouse anti β-tubulin III antibody (Tu-20, Chemicon) or appropriate isotype control. Staining was revealed with a donkey anti mouse IgG FITC conjugated secondary antibody (Biosource). Images were taken using either an inverted Leica DM IRB or Leica DM RA2 microscope. If indicated DAPI nuclear counterstaining was performed using DAPI mounting media (Molecular Probes).

Endoderm Differentiation:

For endoderm differentiation, hESC colonies were dissociated to small aggregates by sequential treatment with collagenase B (Roche) for 45 minutes at 370 C and subsequent treatment with trypsin-EDTA for 3 minutes at 370 C (Cellgro). Following this enzymatic dissociation, the cells were scraped from the plate and gently passed 5 times through a 2 ml pipette, yielding aggregates of 5-10 cells. The aggregates were plated in low adherence culture dishes in StemPro 34 (Invitrogen), supplemented with P/S, Glut, 0.5 mM AA and 4.5×10-4 M MTG. After 3 days EBs were harvested and cultured in 75% (v/v) IMDM, 25% (v/v) Ham's F12 (Invitrogen) supplemented with P/S, Glutamine, 4.5×10-4 M MTG, 0.5 mM AA, 0.5×N2 supplement, 0.5×B27 supplement without Vitamin A and 0.1% albumin (SF-D). Activin A was added at 100 ng/mL. On day 8 EBs were plated on gelatin coated 6 well plates in SF-D, supplemented with human VEGF 5 ng/mL, bFGF 20 ng/mL and human BMP4 50 ng/mL. After a total of 16 days in culture, cells were analyzed by immunohistochemistry for the expression of AFP. To detect AFP, cells were fixed in PBS+4% PFA, blocked with serum free protein block and subsequently stained with rabbit anti-mouse polyclonal AFP antibody (Neomarkers) or the appropriate isotype control. Staining was revealed with a donkey anti rabbit Cy2 conjugated secondary antibody (Jackson Immuno Research). Images were taken using an inverted Leica DM IRB microscope. DAPI nuclear counterstaining was performed where indicated (Molecular Probes).

Mesoderm Differentiation:

Small clumps of undifferentiated hESCs were generated as described above. Clumps were plated in low adherence culture dishes in StemPro 34, supplemented with P/S, Glut, AA and MTG and BMP4 10 ng/mL. After one day bFGF was added at 10 ng/mL. On day 4 media was changed to fresh media containing the following cytokines: VEGF 10 ng/mL, Stem Cell Factor (SCF) 100 ng/mL, erythropoietin (EPO) 4000 U/mL, IL6 10 ng/mL, IL3 20 ng/mL and IL11 5 ng/mL. Three days later the EBs were transferred to IMDM supplemented with plasma derived serum (PDS, Animal Technologies) 5%, protein free hybridoma medium (PFHM-II) 5% (v/v) (Invitrogen), Glut, 0.5 mM AA, 3×10-4 M MTG, VEGF 10 ng/mL, SCF 100 ng/mL, EPO 4000 U/mL, IL6 10 ng/mL, IL3 20 ng/mL and IL11 5 ng/mL, TPO 40 ng/mL and IGF-1 25 ng/mL. Cells were either grown in this media for the remainder of the experiment by changing media every 5-7 days (liquid expansion) or were switched to a methylcellulose based semi-solid media to reveal their colony forming potential.

Methylcellulose Assay:

At day 16 to 18 of mesoderm differentiation, EBs were separated from floating cells by gravity settlement. Both populations were harvested individually to expose only the EB fraction to collagenase type I for 60 minutes, followed by trypsinization for 3 to 10 minutes. After vigorous vortexing cells from the EB fraction were passed 5 times through a 21G needle. Both fraction were then pooled and passed through a cell strainer. Cells were counted and were either analyzed by FACS or plated at a concentration of 50,000 cells/ml of semi-solid media as follows: 1% (m/v) methylcellulose (Fluka), supplemented with P/S, Glut, 15% (v/v) PDS, 5% (v/v) PFHM-II, VEGF 10 ng/mL, SCF 100 ng/mL, EPO 4000 U/mL, GM-CSF 2 ng/mL, IL6 10 ng/mL, IL3 20 ng/mL and IL11 5 ng/mL, TPO 40 ng/mL, IGF-1 25 ng/mL and IMDM to 100%. Colonies were analyzed at day 10 of methylcellulose culture.

Teratoma Formation:

ES cells were dissociated into small aggregates by treatment with collagenase type I for 45 minutes. Following this enzymatic dissociation, the cells were scraped from the plate and gently passed 5 times through a 2 ml pipette, yielding aggregates of 15 to 20 cells. The equivalent of 10,000 cells was resuspended in a 1:1 mixture of IMDM and Matrigel and injected into the hindleg muscle of NOD/SCID mice (The Jackson laboratory). Mice were sacrificed 8-10 weeks later and the teratomas were harvested. Red fluorescent pictures were taken using a stereomicroscope on unfixed tissues. Hind leg muscle was used as a negative control. For flow cytometric analysis the teratoma was cut into small pieces using a scalpel blade and subsequent treatment with Collagenase B for 45 m at 370 C. Cells were then passed several times through a 21 G needle and subsequently treated with Trypsin-EDTA for 5 m. After 2 washes the cells were analyzed on an LSRII flow cytometer. Dead cells were excluded using forward and side scatter parameters. For histological analysis tissue was embedded into paraffin blocks and the sections stained with hematoxylin/eosin (H&E).

Example 1. Identification of hRosa26

Figure 5A:
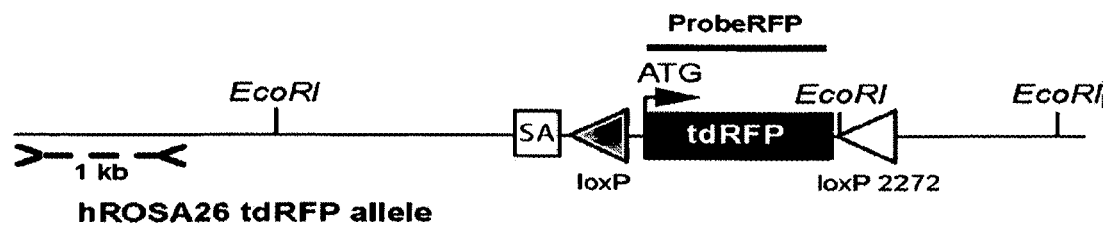
FIG. 5a and FIG. 5b show single integration in the hRosa26 hESC.
Figure 5B:
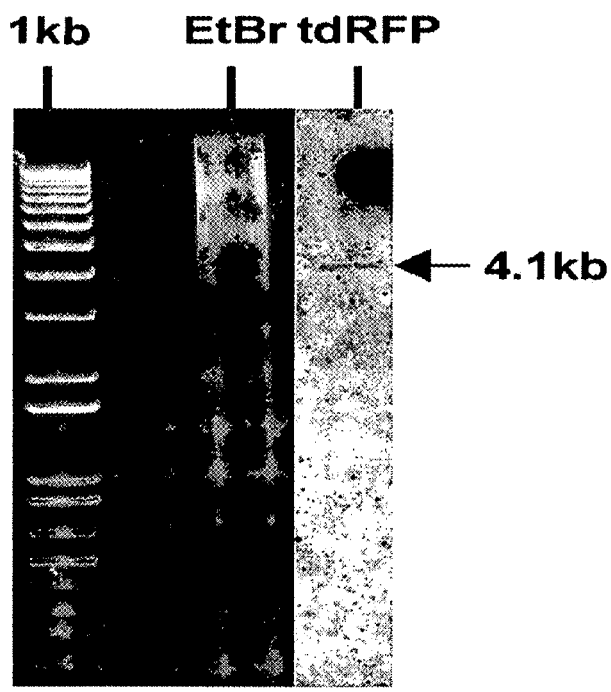

Using the sequence of mouse Rosa26 transcripts (1) as a template to search the Ensembl database (3), a region with several highly significant homologies on human chromosome 3 was located. The highest degree of sequence similarity (>85%) was found in a stretch of non-repetitive DNA corresponding to the 5' portion of exon 1 plus ~1.0 kb of the putative promoter region in the mouse Rosa26 locus (FIG. 5a). An electronic screen of the Ensembl gene expression database for this genomic region revealed a large number of uncharacterized expressed sequence tags (ESTs) and transcripts. These transcripts are derived from a broad spectrum of adult cell types and 3 embryonic stem cell lines. They map to specific positions within the region of Rosa26-synteny, most likely demarcating exons (FIG. 5b). Thus, the region on human chromosome 3 identified represents the equivalent of the mouse Rosa26 locus and should thus be referred to as human Rosa26 (hRosa26).

Figure 1B:
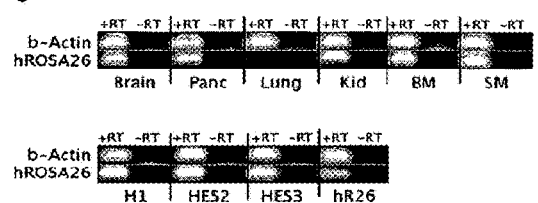

To begin to define the expression pattern of the hRosa26 locus different adult tissues were analyzed for hRosa26 message by quantitative polymerase chain reaction (qPCR) using oligonucleotides against the sequences in putative ExonIII. As shown in FIG. 1a, hRosa26 was expressed in all human tissues tested as well as in 3 different hESC lines. The levels of expression in adult human tissue varied between ~0.2× and ~1.4× of the levels detected in H1 hESCs. Comparable expression patterns were observed using oligonucleotides that span the predicted intron between ExonII and ExonIII in a conventional RTPCR reaction (FIG. 1b). The different levels of expression observed in these human tissues are not unexpected as the mouse Rosa26 locus also shows variable expression in adult tissues.

Example 2. Construction of a hRosa26 Targeting Vector

Figure 1C:
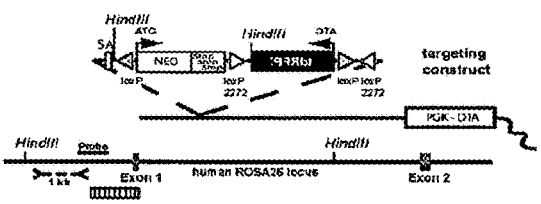
Figure 1D:
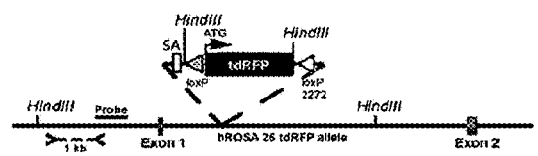

A targeting vector analogous to the widely used mouse Rosa26 vector (2) was constructed (FIG. 1c). The vector contains a 5' short arm and a 3' long arm of homology, which together span approximately 5.1 kb of the hRosa26 locus. The vector overlaps with sequences of the putative first exon and the following intron of the hRosa26 locus. The homologous arms are separated by an expression cassette which consists of several elements, including a viral splice acceptor, followed by a loxP-flanked promoterless neomycin resistance gene. The neomycin gene is followed by an inverted RFP variant (5), termed tandem-dimer RFP (tdRFP), flanked by mutant loxP2272 sites (6). tdRFP is a covalently fused dimer of the genetically modified monomeric RFP. This was selected because it matures fast (about 2 hours) (7), is not toxic in mouse ES cells (8) and is significantly brighter than monomeric RFP variants such as mRFP (1) or mCherry, thus facilitating transgene detection during in vitro differentiation and teratoma formation. The loxP and mutant loxP2272 sites are positioned such that following expression of Cre recombinase (Cre) (9, 10), the neomycin resistance cassette is removed and the tdRFP inverted, placing it under control of the endogenous hRosa26 promoter (FIG. 1d).

Two distinct intermediates can be generated during this process, as recently demonstrated by Luche et al (8). This gene trap construct will function as a Cre inducible fluorescent reporter after successful targeting of the locus. By using an inverted tdRFP cassette rather than a "foxed" stopper cassette (11), the possibility of low levels of "leaky" tdRFP expression detected in previous studies using a similar construct in mouse ES cells was eliminated (8). Furthermore the use of heterotypic loxP sites allows for the subsequent exchange of the tdRFP cassette with virtually any cDNA of interest at the hRosa26 locus using recombinase mediated cassette exchange (RMCE)(12).

Example 3. Gene Targeting

Figure 1E:
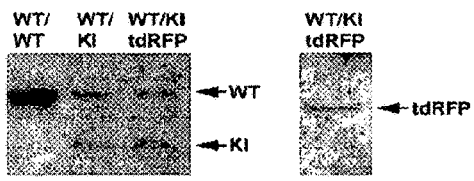
Figure 1F:
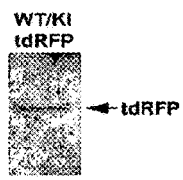

For gene targeting, the hESC line HES213 was electroporated with the linearized targeting construct. One day following electroporation, selection with neomycin sulfate (G418) was initiated. G418 resistant clones, detected 10-12 days later, were picked and analyzed by PCR for evidence of correct targeting using a mock plasmid with an extended 5' homology region as a positive control. Out of 24 clones analyzed one was correctly targeted based on this PCR analysis. This clone was expanded and electroporated with a plasmid that expressed Cre transiently. Forty-eight hours later, tdRFP positive cells, which comprised about 5% of the total population, were isolated by cell sorting and cultured at low density. Colonies expressing tdRFP, identified by fluorescence microscopy, were picked and expanded. Correctly targeted clones were confirmed by Southern blot analysis using an external genomic probe (FIG. 1e). The integration of a single copy of the targeting construct was confirmed by the appearance of a single band of the expected size using a probe specific for the tdRFP cassette (FIG. 1f and FIG. 5). Cre/loxP-mediated deletion of the neomycin cassette and maintenance of the targeted locus was confirmed by loss of G418 resistance and Southern blot analysis (FIG. 1e). One human hRosa26 tdRFP subclone (hRosa26 B7 2.12) was used for most of the subsequent analysis. This clone will be referred to as hRosa26.

Figure 2A:
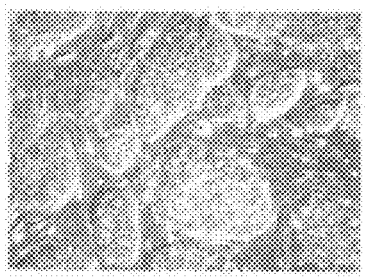
FIG. 2a, FIG. 2b, FIG. 2c, FIG. 2d, FIG. 2e, FIG. 2f, FIG. 2g, FIG. 2h and FIG. 2i show the morphology and differentiation of hRosa26 ES cells.
Figure 2B:
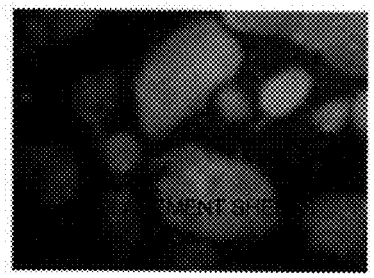
Figure 2C:
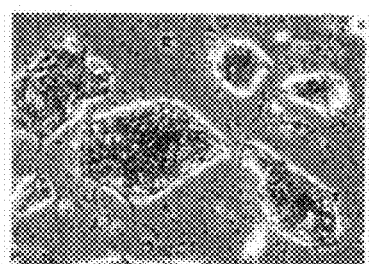
Figure 2D:
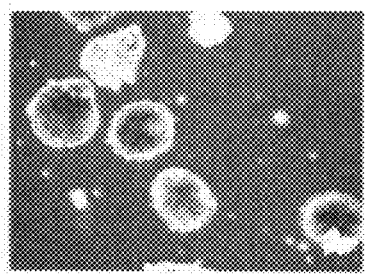
Figure 2E:
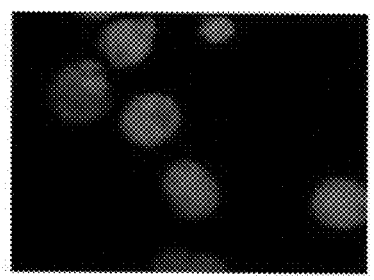
Figure 2F:
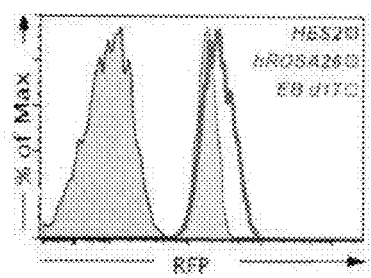
Figure 2G:
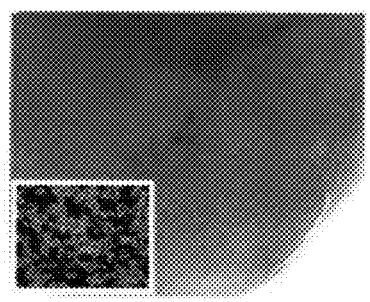
Figure 2H:
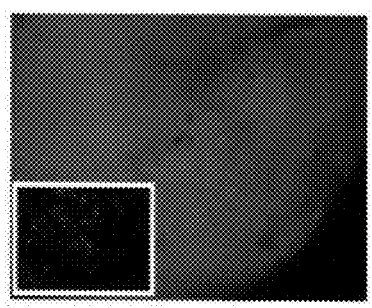
Figure 2I:
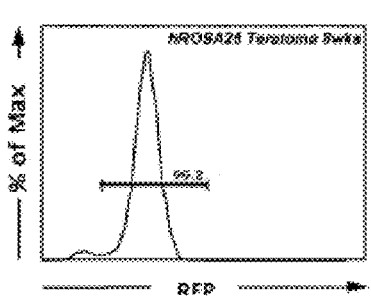
Figure 6A:
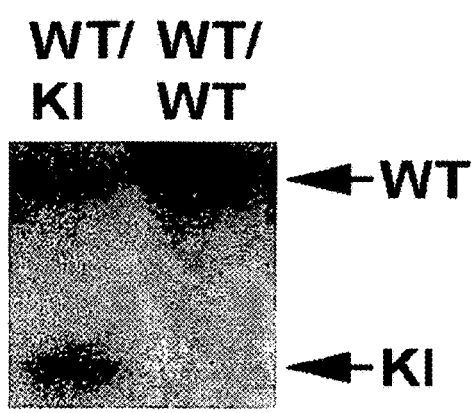
FIG. 6a and FIG. 6b show the identification and characterization of a second hRosa26 clone (hRosa26.2).

From this first set of experiments screening of 40 more clones by Southern blotting revealed no additional, correctly targeted clones (Maximum targeting efficiency 1 in 64, ~1.5%). In a second experiment, one targeted clone was identified (Southern blot) out of 24 clones tested (1 in 24, ~4.2%. overall 2 in 88, ~2.3%). This clone is referred to as hRosa26.2 (FIG. 6a). While the 5 observed targeting frequencies are lower than reported for the mouse Rosa26 locus2, they appear to be in a range well acceptable for multiple targeting experiments. Whether the lower targeting frequency is due to locus-specific species differences with regard to homologous recombination or to more trivial, technical issues, such as suboptimal DNA delivery and selection mechanisms, needs to be investigated in a systematic manner. With only one previous report of gene targeting in hESCs (14) critical parameters for optimization of homologous recombination in human ES cells remains to be determined. Chromosomal analysis of the targeted clone following 8 passages after the second electroporation confirmed a normal karyotype (46XX). The undifferentiated cells displayed a typical ES cell morphology (FIG. 2a), expressed significant levels of tdRFP, readily detectable by fluorescent microscopy (FIG. 2b) and flow cytometric analysis (FIG. 2f). These colonies were positive for alkaline phosphatase (FIG. 2c). When induced to differentiate in serum free media, the hRosa26 tdRFP cells formed embryoid bodies (EBs, FIG. 2d). tdRFP expression could be demonstrated by epifluorescent microscopy (day 4 EBs, FIG. 2e) and flow cytometric analysis at day 17 of differentiation (FIG. 2f). Eight to ten weeks following injection into the hindlimb of NOD/SCID mice, hRosa26 hESCs generated teratomas (FIG. 2g), that grossly expressed tdRFP (FIG. 2h). Immunofluorescent (insert FIG. 2h) and flow cytometric analysis of single cells derived from a second teratoma generated from another hRosa26 subclone (B7 2.10) revealed that most cells (>96%) expressed tdRFP (FIG. 2i).

The small population (<4%) of tdRFP-cells may represent the vasculature of the host. One of the hallmarks of ES cells is their capacity to differentiate to multiple cell types representing derivatives of the 3 germ layers. FIG. 7 shows histological analysis of a hRosa26 hESC-derived teratoma revealing the presence of cartilage and cardiac muscle (mesoderm), ciliated mucosal tissue (endoderm) and neural rosettes (ectoderm).

Example 4. Cell Differentiation Experiments

To monitor tdRFP expression in differentiated progeny generated in vitro, the targeted hESCs were induced to differentiate into cells representing derivatives of the 3 embryonic germ layers ectoderm, endoderm and mesoderm as well as the trophoblast lineage, an extraembryonic population.

Example 4a. Ectoderm Expression

Figure 3A:
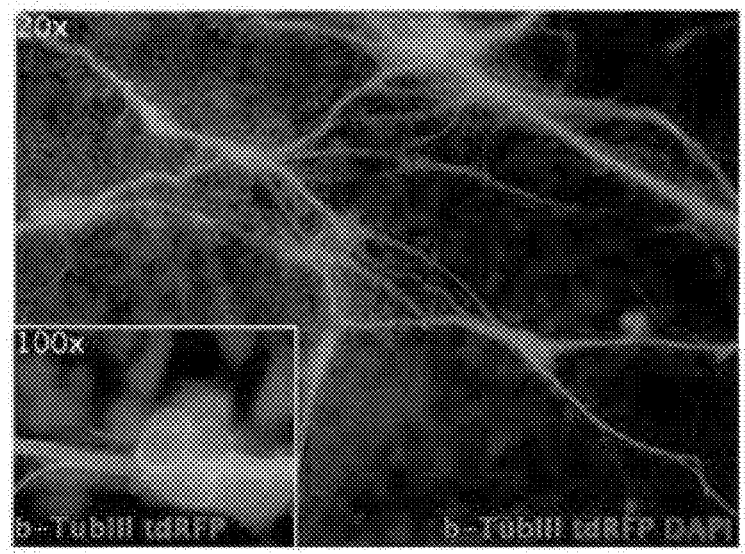
FIG. 3a, FIG. 3b, FIG. 3c, FIG. 3d and FIG. 3e show multilineage differentiation of hRosa26 targeted hESCs in vitro.

To evaluate expression of tdRFP in ectoderm, both wild type and hRosa26 ES cells were induced to differentiate to the neuronal lineage. For this differentiation, the hESCs were removed from the stem cell conditions and differentiated as EBs in serum free media. Basic fibroblast growth factor (bFGF) was added to the EB cultures at day 4 of differentiation and at day 6 the EBs were transferred to gelatin coated 6-well-plates and cultured for an additional 21 days in serum-free media supplemented with epidermal growth factor (EGF). These conditions supported the development of cells that express the neuronal marker β-Tubulin III15. These β-Tubulin III+ neuronal cells retained tdRFP expression (FIG. 3a, insert) demonstrating that the human Rosa26 locus remains active following differentiation of hESCs to neuroectoderm. The HES2 parental cell line generated β-Tubulin III+ neurons that did not exhibit red fluorescence. Neuronal cells generated from both the hRosa26 and wild type cells also expressed the neural cell adhesion molecule (NCAM).

Example 4b. Endoderm Expression

Figure 3C:
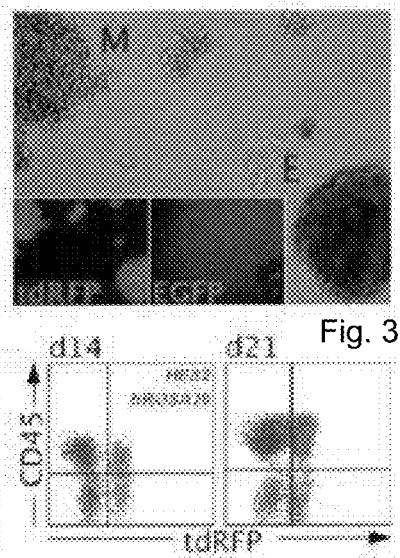
Figure 3D:
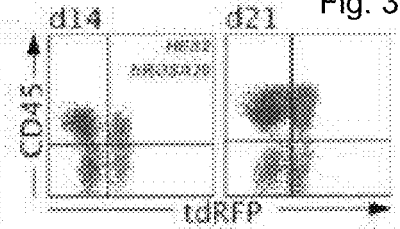
Figure 3B:
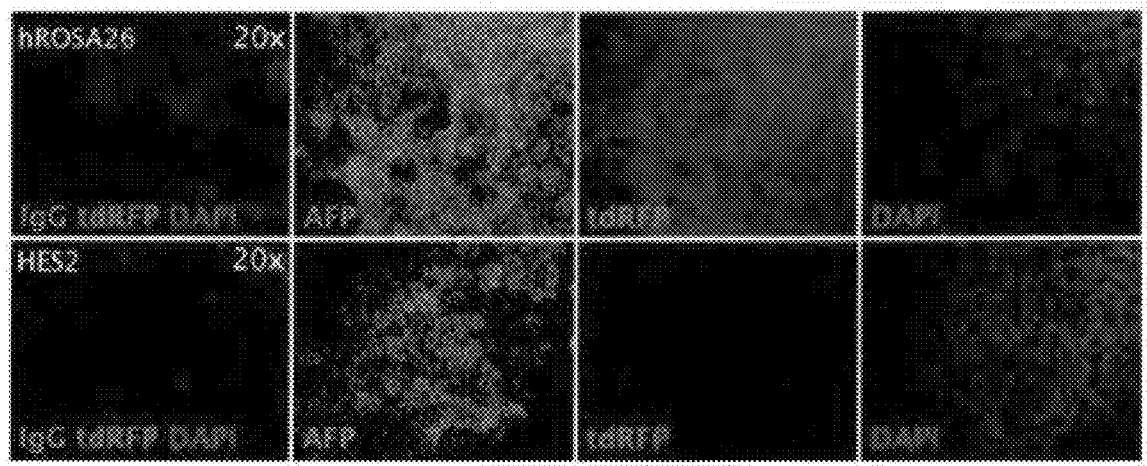

It has been shown that activin A can induce definitive endoderm from mouse ES cells in the absence of serum (16). D'Amour et al. recently showed that this factor also functions to induce endoderm in hESCs cultures (17, 18). To test the endoderm potential of the hRosa26 targeted hESCs they were differentiated as EBs in serum free conditions in the presence of activin A. Following 8 days of induction the EBs were transferred to gelatin coated 6-well plates in serum free medium containing vascular endothelial growth factor (VEGF), basic fibroblast growth factor (bFGF) and bone morphogenic protein 4 (BMP4). These factors have been shown to be important for liver specification in the mouse embryo (19) and mouse embryonic stem cell differentiation cultures (20). Clusters of albumin and alpha-fetoprotein (AFP) positive cells could be detected following 16 days of culture. As shown in FIG. 3b, the AFP-expressing cells generated from the Rosa26 targeted hESCs exhibited bright red fluorescence whereas those from the parental cell line did not. These findings indicate that the human Rosa26 locus is also expressed in endoderm derived cell populations.

Example 4c. Mesoderm Expression

Figure 6B:
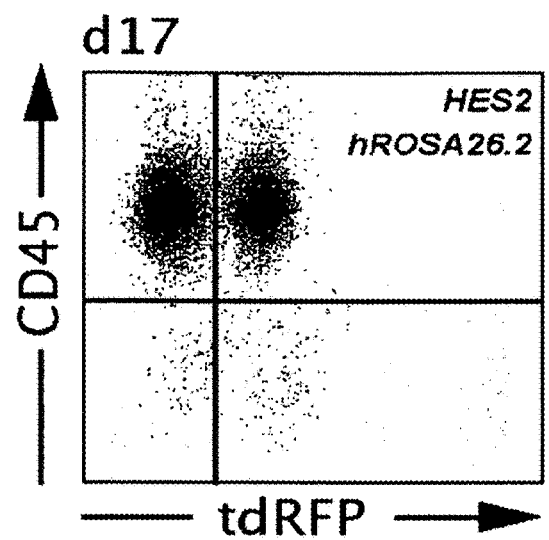
Figure 7A:
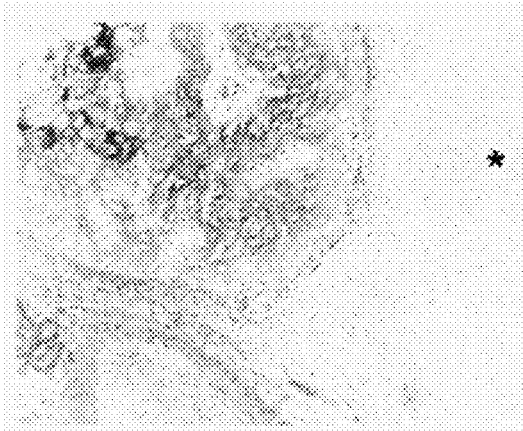
FIG. 7a, FIG. 7b, FIG. 7c and FIG. 7d show a histological analysis of hRosa26-derived teratoma ES cells injected into the hindleg muscle of NOD/SCID mice and resulting teratomas were analyzed 9 weeks later. Hematoxylin/eosin (H&E) stained paraffin sections from these teratomas demonstrate contribution to all 3 germ 20 layers.
Figure 7B:
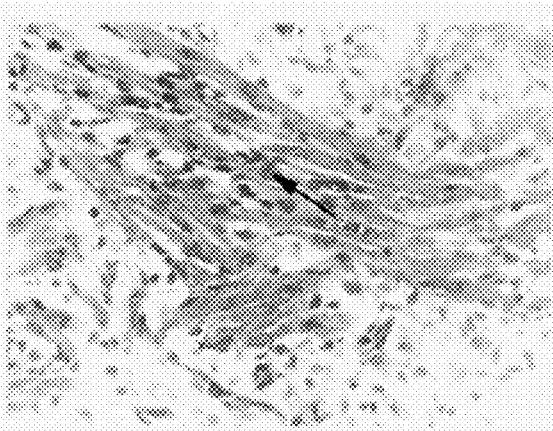
Figure 7C:
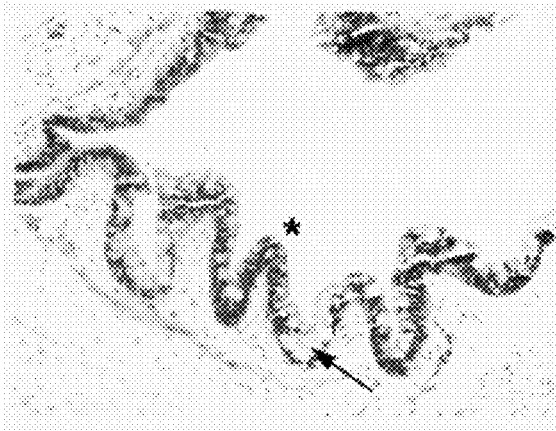
Figure 7D:
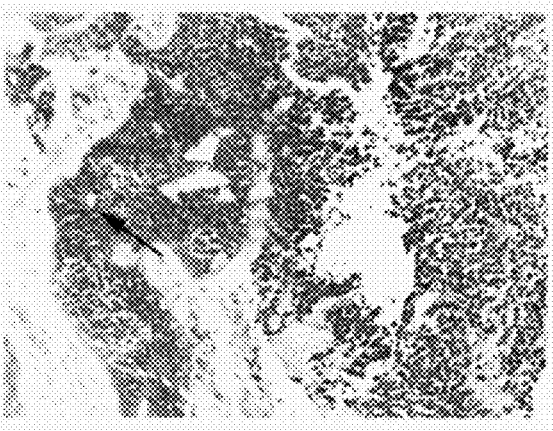

To evaluate expression in mesoderm derivatives, the Rosa26 targeted hESCs were differentiated to the hematopoietic lineage by induction with BMP4 in serum free medium (21, 22). At day 18, EBs were dissociated and replated into methylcellulose containing a broad spectrum of hematopoietic cytokines, conditions that will support the development of both erythroid and myeloid hematopoietic colonies. As shown in FIG. 3c, both types of colonies expressed tdRFP. CD45, a pan specific hematopoietic marker, is expressed on hematopoietic cells at days 14 and 21 of EB differentiation (FIG. 3d). At these time points both CD45– and CD45+ cells released into the culture medium expressed tdRFP. The parental wild type hESCs derived cells were tdRFP negative. The second targeted cell line, hRosa26.2 also generated CD45+ cells that express high levels of tdRFP following induction with BMP4 (FIG. 6b).

Example 4d. Expression of tdRFP in an Extraembryonic Population

Figure 3E:
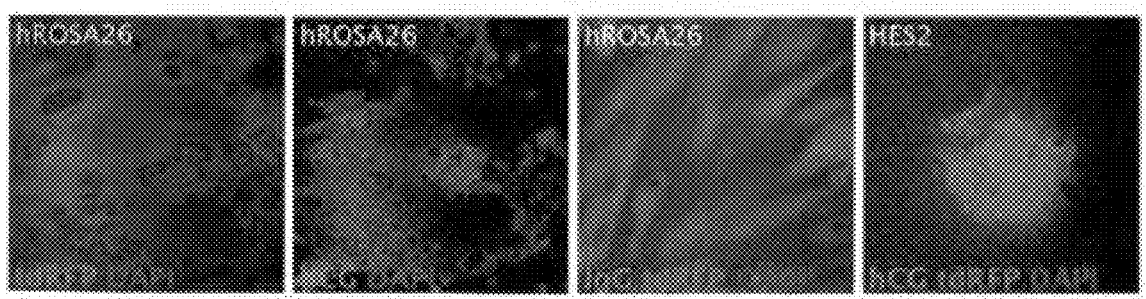
Figure 4B:
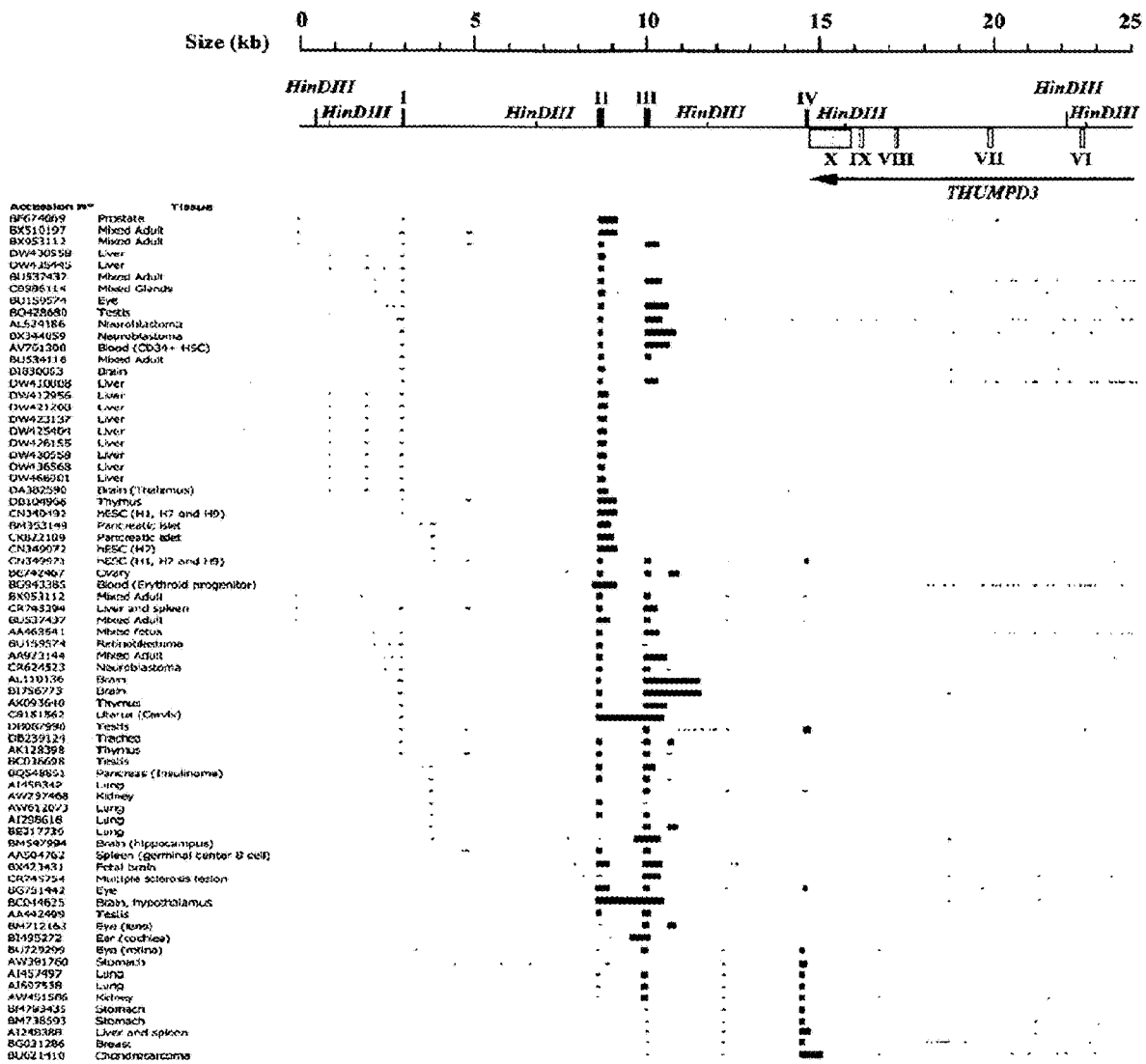

To test the expression of tdRFP in an extraembryonic population, wild type and hRosa26 hESC were induced to differentiate to the trophoblast lineage by treatment with high levels of human recombinant BMP423. As shown in FIG. 3e derivatives of both the parental HES2 (right) and the targeted hRosa26 (left) hESCs were able generate cells that secret human chorionic gonadotropin. Only those generated from the targeted hESC line expressed tdRFP. Taken together, these findings clearly demonstrate that the hRosa26 locus is expressed in derivatives of all three germ layers as well as in trophoblast cells generated in culture.

Example 5. RMCE

Figure 8A:
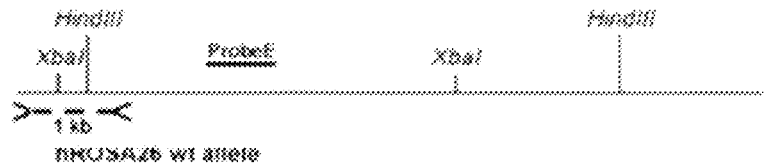
FIG. 8a, FIG. 8b, FIG. 8c, FIG. 8d and FIG. 8e show RMCE in hRosa26 ES cells.
Figure 8B:
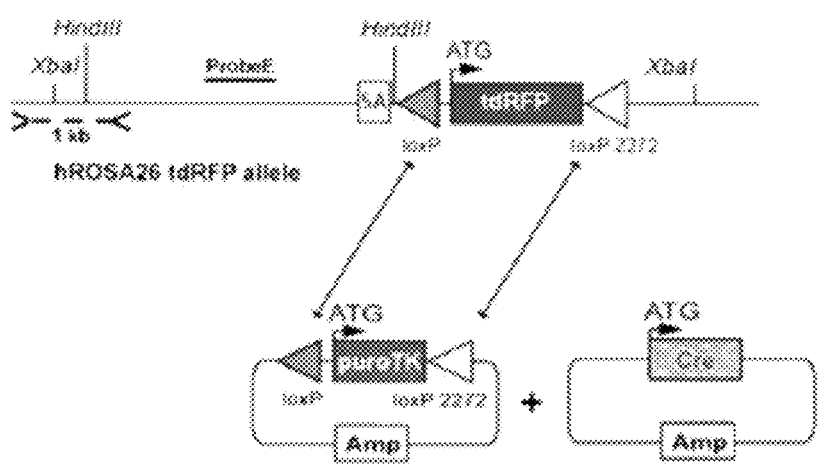
Figure 8C:
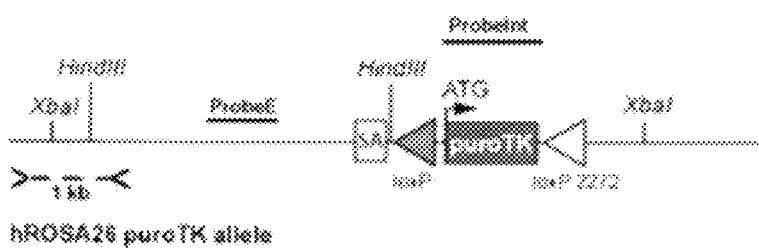
Figure 8D:
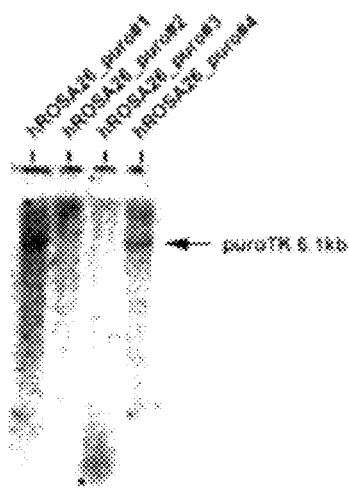
Figure 8E:
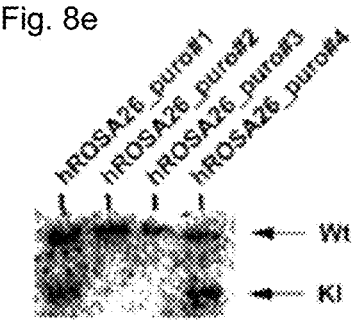

The targeted insertion of loxP sites along with tdRFP introduced a homing site for subsequent RMCE—a method that would allow the insertion of any sequence of interest into the hRosa26 locus without the need of gene targeting or drug selection. To test the feasibility of this approach in hESCs, an exchange vector was engineered containing a promoterless puromycin resistance cassette (puro) flanked by a 5' loxP and a 3' loxP2272 site (FIG. 8b). This exchange vector, together with a Cre expression plasmid was electroporated into one hRosa26 clone. Forty eight hours later, tdRFP negative cells (those that lost the tdRFP insert) were isolated by cell sorting and cultured on MEF cells in the absence of any drug selection. Approximately 20 clones grew from 10.000 tdRFP-sorted cells within 14 day of culture. Four of these 20 clones were tdRFP negative as determined by epifluorescent microscopy and of these, 2 were resistant to puromycin. It is unclear why the majority of the clones generated from the tdRFP-cells consistently regained tdRFP expression. One possibility is that the tdRFP coding sequence re-inserted into the site following Cre excision, and in doing so, established the original confirmation of the locus. The physical organization of the targeted locus was analyzed in the 4 tdRFP negative clones (hRosa26_puro #1–4). Southern blot analysis revealed that the 2 puromycin resistant clones (hRosa26_puro #1+4) each contained the predicted band indicative of a single integration of the puromycin cassette following hybridization with a puro specific internal probe (FIG. 8d). Both the wild type and targeted alleles were detected following hybridization with an external probe (FIG. 8e). The 2 tdRFP-clones (hRosa26_puro #2+3) that were sensitive to puromycin lost the targeted allele, presumably due to homologous recombination mediated repair by the sister chromosome after the Cre induced double strand break. Neither of these clones contained a detectable puromycin specific band in a Southern blot analysis (FIG. 8d). This exchange in the two puromycin-positive clones was not driven by a selection with antibiotics, but rather was dependant on the loss of tdRFP, illustrating the potential of this method as a universal strategy to exchange tdRFP with otherwise non-selectable genes. Subsequently, two additional exchange vectors were designed, one expressing EGFP and the other LHX224. Preliminary analysis with these vectors indicate an exchange frequency of 1 in 9 and 3 in 5 of the tdRFP-clones, respectively. Improving DNA delivery conditions and varying the ratio of exchange plasmid to Cre expression plasmid may further improve the favored outcome. Together these findings clearly demonstrate that it is possible to introduce cDNA's of interest into the hRosa26 lcous of the Rosa26 hESC through RMCE.

REFERENCES

1. Zambrowicz, B. P. et al. Disruption of overlapping transcripts in the ROSA beta geo 26 gene trap strain leads to widespread expression of betagalactosidase in mouse embryos and hematopoietic cells. Proc Natl Acad Sci USA 94, 3789-94 (1997).
2. Soriano, P. Generalized lacZ expression with the ROSA26 Cre reporter strain. Nat Genet 21, 70-1 (1999).
3. Birney, E. et al. Ensembl 2006. Nucleic Acids Res 34, D556-61 (2006).
4. Friedrich, G. & Soriano, P. Promoter traps in embryonic stem cells: a genetic screen to identify and mutate developmental genes in mice. Genes Dev 5, 1513-23 (1991).
5. Campbell, R. E. et al. A monomeric red fluorescent protein. Proceedings of the National Academy of Sciences of the United States of America 99, 7877 (2002).
6. Siegel, R. W., Jain, R. & Bradbury, A. Using an in vivo phagemid system to identify non-compatible loxP sequences. FEBS Lett 499, 147-53 (2001).

7. Shaner, N. C. et al. Improved monomeric red, orange and yellow fluorescent proteins derived from *Discosoma* sp. red fluorescent protein. Nat Biotechnol 22, 1567-72 (2004).
8. Luche, H., Weber, O., Rao, T. R., Blum, C. & Fehling, H. J. Faithful activation of an extra-bright red fluorescent protein in "knock-in" Cre-reporter mice ideally suited for lineage tracing studies. Eur J Immunol 37, in press (2007).
9. Schnutgen, F. et al. A directional strategy for monitoring Cre-mediated recombination at the cellular level in the mouse. Nat Biotechnol 21, 562-5 (2003).
10. Sternberg, N. & Hamilton, D. Bacteriophage P1 site-specific recombination. I. Recombination between loxP sites. J Mol Biol 150, 467-86 (1981).
11. Mao, X., Fujiwara, Y., Chapdelaine, A., Yang, H. & Orkin, S. H. Activation of EGFP expression by Cre-mediated excision in a new ROSA26 reporter mouse strain. Blood 97, 324-6 (2001).
12. Bouhassira, E. E., Westerman, K. & Leboulch, P. Transcriptional behavior of LCR enhancer elements integrated at the same chromosomal locus by recombinase-mediated cassette exchange. Blood 90, 3332-44 (1997).
13. Reubinoff, B. E., Pera, M. F., Fong, C. Y., Trounson, A. & Bongso, A. Embryonic stem cell lines from human blastocysts: somatic differentiation in vitro. Nat Biotechnol 18, 399-404 (2000).
14. Zwaka, T. P. & Thomson, J. A. Homologous recombination in human embryonic stem cells. Nat Biotechnol 21, 319-21 (2003).
15. Reubinoff, B. E. et al. Neural progenitors from human embryonic stem cells. Nat Biotechnol 19, 1134-40 (2001).
16. Kubo, A. et al. Development of definitive endoderm from embryonic stem cells in culture. Development 131, 1651-62 (2004).
17. D'Amour, K. A. et al. Efficient differentiation of human embryonic stem cells to definitive endoderm. Nat Biotechnol 23, 1534-41 (2005).
18. D'Amour, K. A. et al. Production of pancreatic hormone-expressing 22 endocrine cells from human embryonic stem cells. Nat Biotechnol 24, 1392-401 (2006).
19. Rossi, J. M., Dunn, N. R., Hogan, B. L. & Zaret, K. S. Distinct mesodermal signals, including BMPs from the septum transversum mesenchyme, are required in combination for hepatogenesis from the endoderm. Genes Dev 15, 1998-2009 (2001).
20. Gouon-Evans, V. et al. BMP-4 is required for hepatic specification of mouse embryonic stem cell-derived definitive endoderm. Nat Biotechnol 24, 1402-11 (2006).
21. Johansson, B. M. & Wiles, M. V. Evidence for involvement of activin A and bone morphogenetic protein 4 in mammalian mesoderm and hematopoietic development. Mol Cell Biol 15, 141-51 (1995).
22. Kennedy, M., D'Souza, S. L., Lynch-Kattman, M., Schwantz, S. & Keller, G. Development of the hemangioblast defines the onset of hematopoiesis in human ES cell differentiation cultures. Blood (2006).
23. Xu, R. H. et al. BMP4 initiates human embryonic stem cell differentiation to trophoblast. Nat Biotechnol 20, 1261-4 (2002).
24. Xu, Y. et al. LH-2: a LIM/homeodomain gene expressed in developing lymphocytes and neural cells. Proc Natl Acad Sci USA 90, 227-31 (1993).
25. Costa, M. et al. The hESC line Envy expresses high levels of GFP in all differentiated progeny. Nat Methods 2, 259-60 (2005).
26. Nolden, L. et al. Site-specific recombination in human embryonic stem cells induced by cell-permeant Cre recombinase. Nat Methods 3, 461-7 (2006).
27. Gerrard, L., Zhao, D., Clark, A. J. & Cui, W. Stably transfected human embryonic stem cell clones express OCT4-specific green fluorescent protein and maintain self-renewal and pluripotency. Stem Cells 23, 124-33 (2005).
28. Muotri, A. R., Nakashima, K., Toni, N., Sandler, V. M. & Gage, F. H. Development of functional human embryonic stem cell-derived neurons in mouse brain. Proc Natl Acad Sci USA 102, 18644-8 (2005).
29. Thomson, J. A. et al. Embryonic stem cell lines derived from human blastocysts. Science 282, 1145-7 (1998).
30. Kennedy, M. & Keller, G. M. Hematopoietic commitment of ES cells in culture. Methods Enzymol 365, 39-59 (2003).

We claim:

1. A targeting vector comprising an expression cassette comprising a nucleic acid encoding a protein, wherein said nucleic acid is heterologous to a human Rosa 26 gene, said expression cassette flanked by DNA sequences homologous to the human Rosa26 gene.

2. The targeting vector of claim 1 wherein the expression cassette further comprises a promoter operably linked to the nucleic acid encoding the protein.

3. The targeting vector of claim 2 wherein the promoter is selected from the group consisting of a constitutive ubiquitous promoter, a constitutive tissue specific promoter, an inducible ubiquitous promoter and an inducible tissue specific promoter.

4. The targeting vector of claim 2 wherein the promoter is heterologous to the human Rosa26 gene.

5. The targeting vector of claim 2 wherein the promoter is the endogenous human Rosa26 promoter.

6. The targeting vector of claim 1 wherein the sequences homologous to the human Rosa26 gene are derived from the 5' and 3' flanking arms of the human Rosa26 gene.

7. The targeting vector of claim 1 further comprising tags for protein detection, enhancers, selection markers, and combinations thereof.

8. The targeting vector of claim 1 wherein the nucleic acid encodes a recombinase or a reporter.

9. The targeting vector of claim 1 wherein the expression cassette further comprises a marker gene, one or more recombinase recognition sites, a poly A signal, an intron, or combinations thereof.

10. The targeting vector of claim 1 wherein the expression cassette further comprises a viral splice acceptor, a loxP-flanked promoterless neomycin resistance gene, an inverted RFP variant, loxP2272 sites, or combinations thereof.

11. The targeting vector of claim 1 wherein the expression cassette comprises the following elements in sequential order: (a) a viral splice acceptor, (b) a loxP site, (c) a promoterless neomycin resistance gene, (d) a loxP2272 site, (e) an inverted nucleic acid sequence encoding the protein, (f) a loxP site, and (g) a loxP2272 site.

* * * * *